(12) United States Patent
Stearns et al.

(10) Patent No.: US 9,375,539 B2
(45) Date of Patent: Jun. 28, 2016

(54) MULTIMODAL SURGICAL GAS DELIVERY SYSTEM FOR LAPAROSCOPIC SURGICAL PROCEDURES

(75) Inventors: Ralph Stearns, Bozrah, CT (US); Dennis Feldman, Apollo Beach, FL (US); Raymond Y. Tang, New Haven, CT (US)

(73) Assignee: SurgiQuest, Inc., Milford, CT (US)

( * ) Notice: Subject to any disclaimer, the term of this patent is extended or adjusted under 35 U.S.C. 154(b) by 771 days.

(21) Appl. No.: 13/237,628

(22) Filed: Sep. 20, 2011

(65) Prior Publication Data
US 2012/0150101 A1 Jun. 14, 2012

Related U.S. Application Data

(60) Provisional application No. 61/384,412, filed on Sep. 20, 2010.

(51) Int. Cl.
*A61M 13/00* (2006.01)
*A61B 17/34* (2006.01)
(Continued)

(52) U.S. Cl.
CPC .......... *A61M 13/003* (2013.01); *A61B 17/3421* (2013.01); *A61B 17/3474* (2013.01); *A61M 1/0031* (2013.01); *A61M 13/00* (2013.01); *A61M 13/006* (2014.02); *B01D 46/0008* (2013.01); *B01D 46/4254* (2013.01);
(Continued)

(58) Field of Classification Search
CPC .......... A61B 17/3421; A61B 17/3474; A61B 2017/00221; A61B 2017/00225; A61B 2019/448; A61B 2019/464; A61B 2218/008; A61M 13/00; A61M 13/006; B01D 46/0008; B01D 46/4254

USPC ................................................. 604/23, 24, 26
See application file for complete search history.

(56) References Cited

U.S. PATENT DOCUMENTS 4,735,603 A     4/1988  Goodson et al.
5,788,688 A *  8/1998  Bauer et al. ........................ 606/1
(Continued)

FOREIGN PATENT DOCUMENTS

DE     4219859 A1    12/1993
EP     2482869 A1    8/2012
(Continued)

OTHER PUBLICATIONS

Supplemental Search Report issued Sep. 8, 2014 in connection with EP Application No. 11827365.

*Primary Examiner* — Imani Hayman
(74) *Attorney, Agent, or Firm* — Locke Lord LLP; Scott D. Wofsy

(57) ABSTRACT

The subject multimodal surgical gas delivery system configured to couple to one or more surgical devices providing access into a patient body cavity includes a computer-controlled control unit configured and adapted to provide at least one of the following modes of operation. A first mode of operation for providing a pressurized insufflation fluid from an insufflation gas source into a surgical device for providing and maintaining sealable access to the body cavity in a surgical device. A second mode of operation for performing smoke evacuation in a filter element from insufflation fluid caused to recycle through the multimodal system from the body cavity via a surgical device. A third mode of operation for providing insufflation fluid from the insufflation gas source into the body cavity for creating and maintaining insufflation of the body cavity.

8 Claims, 37 Drawing Sheets

(51) Int. Cl.
*B01D 46/00* (2006.01)
*B01D 46/42* (2006.01)
*A61M 1/00* (2006.01)
*A61B 17/00* (2006.01)

(52) U.S. Cl.
CPC ............... *A61B 2017/00221* (2013.01); *A61B 2017/00225* (2013.01); *A61B 2218/008* (2013.01); *A61M 2205/33* (2013.01); *A61M 2205/70* (2013.01); *A61M 2205/75* (2013.01)

(56) References Cited

U.S. PATENT DOCUMENTS

| | | | |
|---|---|---|---|
| 7,182,752 B2 | 2/2007 | Stubbs et al. | |
| 7,285,112 B2 | 10/2007 | Stubbs et al. | |
| 7,338,473 B2 | 3/2008 | Campbell et al. | |
| 7,413,559 B2 | 8/2008 | Stubbs et al. | |
| 7,761,188 B2* | 7/2010 | Palmerton et al. | 700/282 |
| 7,854,724 B2 | 12/2010 | Stearns et al. | |
| 2005/0000196 A1* | 1/2005 | Schultz | 55/385.2 |
| 2007/0163585 A1* | 7/2007 | Uesugi | A61M 13/003 128/204.18 |
| 2007/0249990 A1 | 10/2007 | Cosmescu | |
| 2009/0137943 A1* | 5/2009 | Stearns et al. | 604/26 |
| 2009/0278065 A1* | 11/2009 | Grenaway | A61M 13/003 251/61 |

FOREIGN PATENT DOCUMENTS

| | | |
|---|---|---|
| WO | WO-2010/042204 A2 | 4/2010 |
| WO | WO-201141387 A1 | 4/2011 |

* cited by examiner

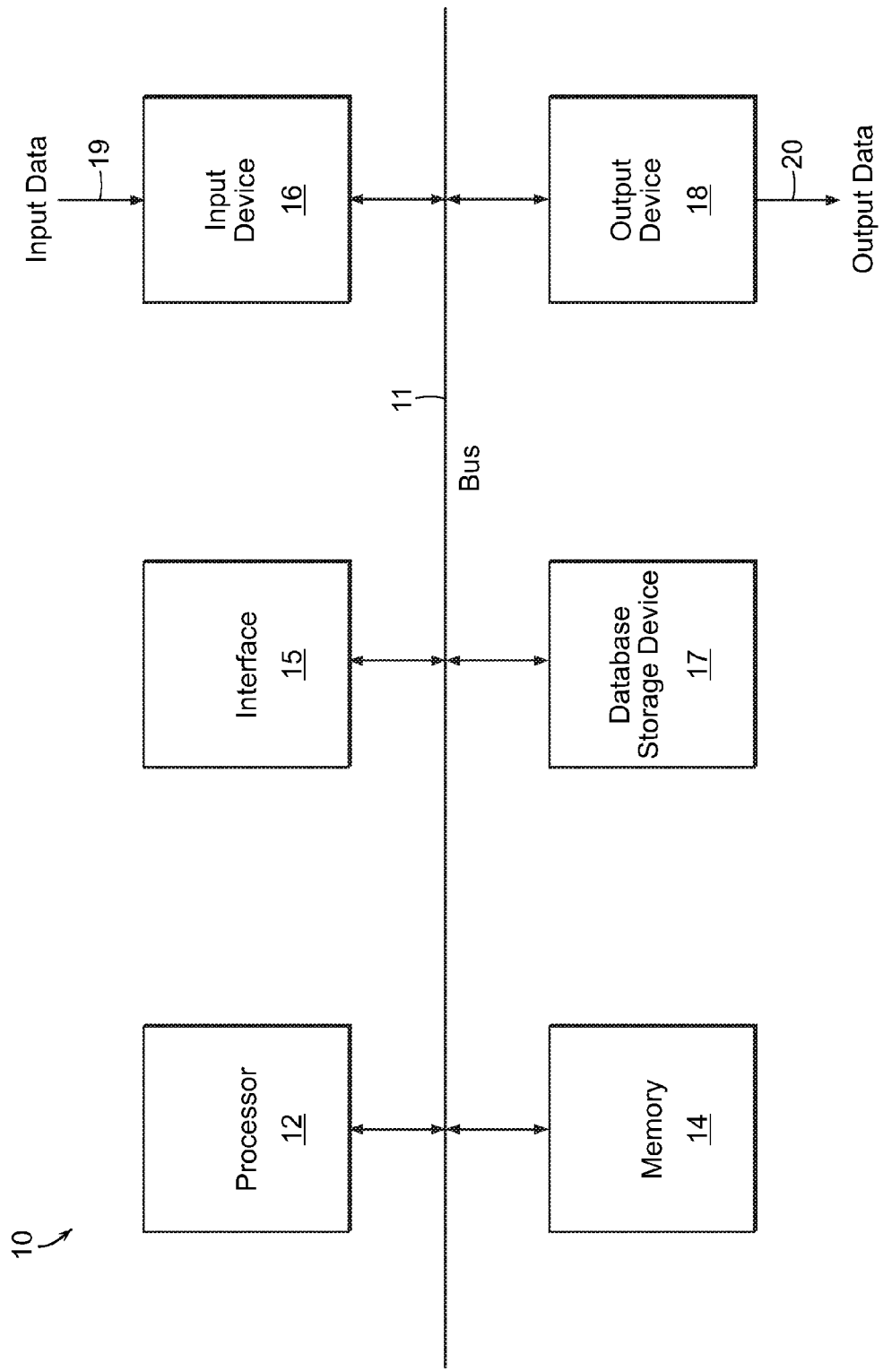

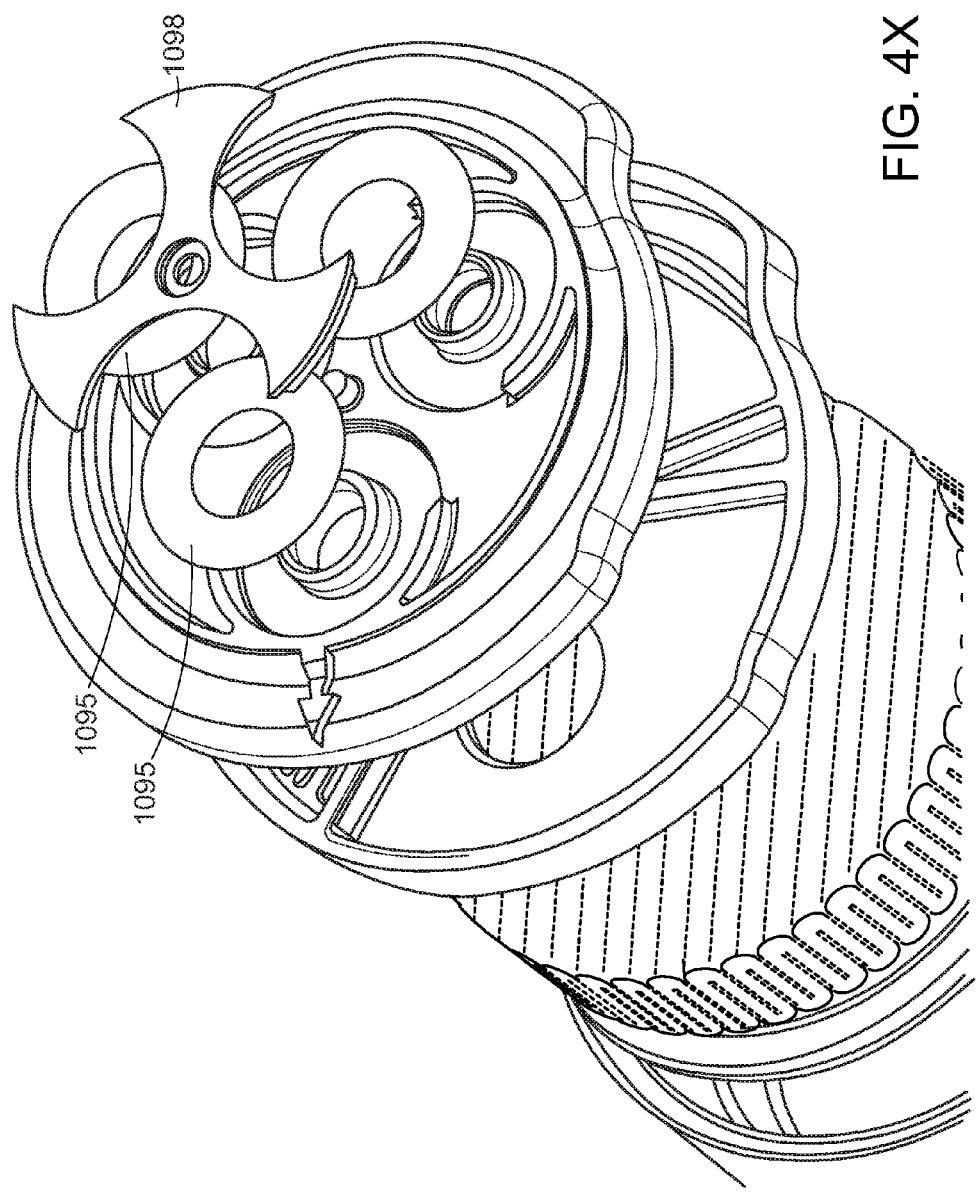

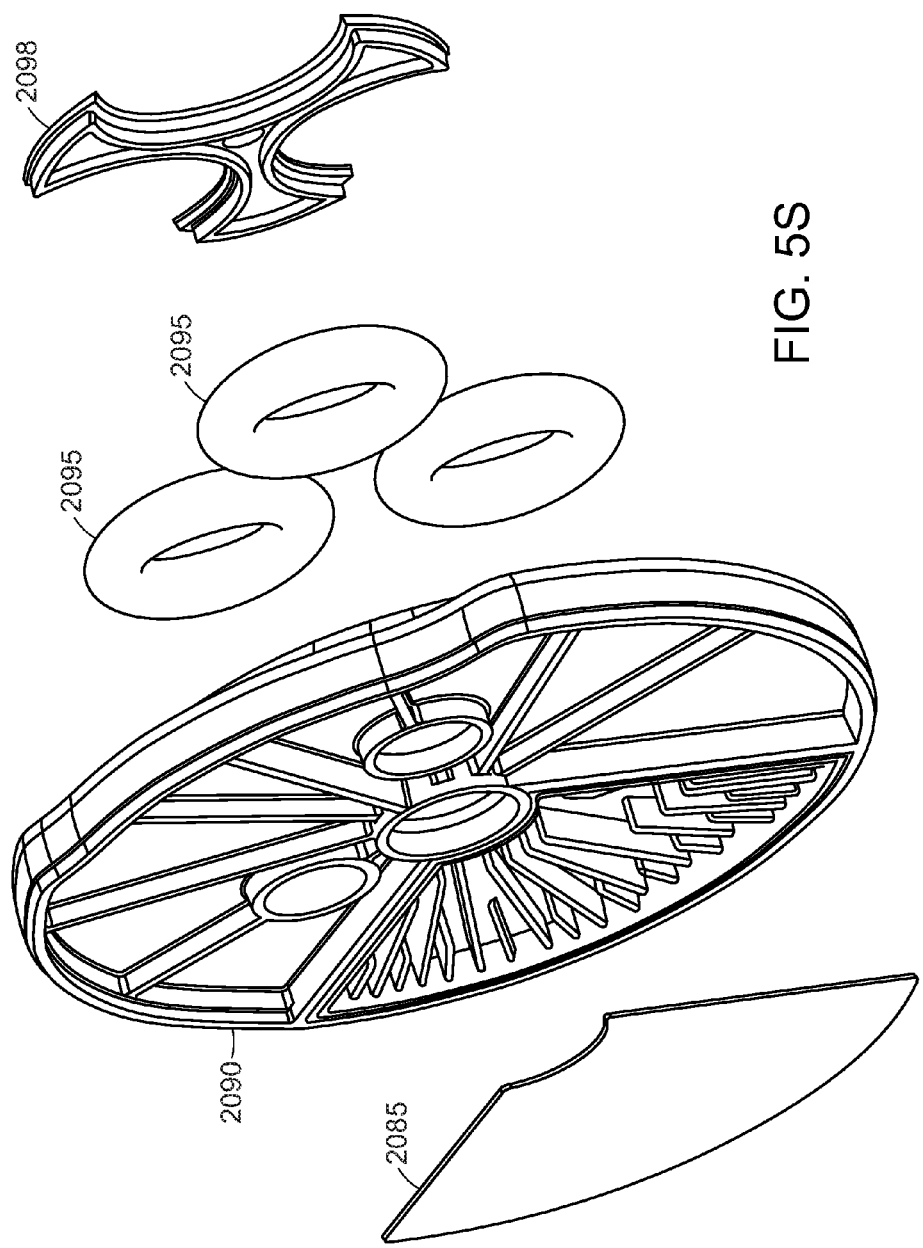

MULTIMODAL SURGICAL GAS DELIVERY SYSTEM FOR LAPAROSCOPIC SURGICAL PROCEDURES

CROSS-REFERENCE TO RELATED APPLICATIONS

This application claims priority to U.S. Patent Application Ser. No. 61/384,412 filed Sep. 20, 2010 and is also related to U.S. Patent Application Ser. No. 61/246,921, filed Sep. 29, 2009 and U.S. patent application Ser. No. 12/577,188, filed Oct. 11, 2009. This application is additionally related to U.S. Pat. Nos. 7,182,752; 7,285,112; 7,413,559; and 7,338,473, U.S. or PCT Patent Application Serial Numbers: U.S. Ser. No. 11/517,929, filed Sep. 8, 2006 (U.S. Pub. No. 2007/0088275); PCT/US07/88017, filed Dec. 18, 2007 (Pub. No. WO 2008/077080); U.S. Ser. No. 11/960,701, filed Dec. 20, 2007 (U.S. Pub. No. 2009/0137943); U.S. 61/104,448, filed Oct. 10, 2008; U.S. 61/195,898, filed Oct. 10, 2008; and U.S. Ser. No. 12/148,234, filed Apr. 17, 2008 (U.S. Pub. No. 2008/0262302). Each of the foregoing documents is incorporated herein by reference in its entirety.

FIELD OF THE INVENTION

The present invention relates to surgical insufflation systems, and surgical smoke evacuation systems. Particularly, the present invention is directed to a multimodal system capable of surgical insufflation, smoke evacuation and recirculation of insufflation gasses, and to related methods and devices.

BACKGROUND OF THE INVENTION

Laparoscopic, or "minimally invasive" surgical techniques are becoming increasingly more common. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery an other techniques (e.g. harmonic scalpels) create smoke and other debris in the surgical cavity, reducing visibility by fogging the view from, and coating surfaces of endoscopes and the like.

A variety of surgical insufflation systems and smoke evacuation systems are known in the art. Additionally, SurgiQuest, Inc., Orange, Conn. USA has developed surgical access devices that permit access to an insufflated surgical cavity without conventional mechanical seals, and has developed related systems for providing sufficient pressure and flow rates to such access devices, as described in whole or in part in U.S. Patent Publication No. 2007/0088275, as well as in U.S. Patent Application Ser. No. 61/104,448, filed Oct. 10, 2008, for example.

The present invention relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described in U.S. Patent Publication No. 2007/0088275, as well as those in U.S. Pat. Nos. 7,182,752, 7,285,112, 7,413,559 or 7,338,473, for example.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

To achieve these and other advantages and in accordance with the purpose of the invention, as embodied, the invention includes, in one aspect, a multimodal surgical gas delivery system having a fluid pump, supply conduit, return conduit, adjustable back-pressure control valve, insufflation control and conduit, a pressure sensor and a conduit set. The fluid pump is adapted and configured to circulate insufflation fluid through the system. The supply conduit is in fluid communication with an output of the fluid pump and is configured and adapted for delivering pressurized insufflation fluid to an output port of the control unit. The return conduit is in fluid communication with an input of the fluid pump for delivering insufflation fluid to the fluid pump and is configured and adapted for returning insufflation fluid to an input port of the control unit. The adjustable back-pressure control valve is in fluid communication with the supply conduit and the return conduit, and is adapted and configured to respond to a supply conduit pressure exceeding a set pressure by opening and directing fluid from the supply conduit to the return conduit. The insufflation control controls addition of insufflation fluid into the system, from an insufflation gas source. The insufflation conduit delivers insufflation gas to the system from the insufflation control. The pressure sensor is adapted and configured to sense pressure of a surgical cavity through the insufflation conduit. The control panel is configured and adapted to permit a user to select a mode of the multimodal surgical gas delivery system. The conduit set is adapted and configured to connect to the supply, return and insufflation conduits, and to a plurality of surgical devices in fluid communication with the surgical cavity.

The subject systems can further include a switching valve in connection with the supply, return and insufflation conduits, configured and adapted to divert the insufflation conduit between fluid connection with one or more of the surgical devices, and the return conduit to the fluid pump. The insufflation conduit can serve as a conduit for detecting abdominal pressure and can also further include a conduit for detecting abdominal pressure, separate from the insufflation conduit.

In another aspect, the invention includes a multimodal surgical gas delivery system configured to couple to one or more surgical devices providing access into a patient body cavity. The system includes a computer-controlled control unit configured and adapted to provide at least one of the following modes of operation: a first mode of operation for providing a pressurized insufflation fluid from an insufflation gas source into a surgical device for providing and maintaining sealable access to the body cavity in a the surgical device; and a second mode of operation for performing smoke evacuation in a filter element from insufflation fluid caused to recycle through the multimodal system from the body cavity via a said surgical device. In a further aspect, the computer-controlled control unit is further configured and adapted to provide a third mode of operation for providing insufflation fluid from the insufflation gas source into the body cavity for creating and maintaining insufflation of the body cavity.

Additionally, a control panel is provided and coupled to the computer-controlled control unit and is configured and adapted to permit a user to select an aforesaid mode of operation for the multimodal surgical gas delivery system. The control panel may be further configured and adapted to permit a user to selectively adjust operation parameters of each of the modes of operation for the multimodal surgical gas delivery system.

It is to be understood that both the foregoing general description and the following detailed description are exemplary and are intended to provide further explanation of the invention.

BRIEF DESCRIPTION OF THE DRAWINGS

The accompanying drawings, which are incorporated in and constitute part of this specification, are included to illustrate and provide a further understanding of the systems, devices and related methods of the invention. Together with the description, the drawings serve to explain the principles of the invention, wherein:

FIG. 1A is a system level diagram of a computering environment used by the present invention;

DETAILED DESCRIPTION

Reference will now be made in detail to select embodiments of the invention, examples of which are illustrated in the accompanying drawings. The invention is now described more fully with reference to the accompanying drawings, in which illustrated embodiments of the invention are shown. The present invention is not limited in any way to the illustrated embodiments as the illustrated embodiments described below are merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the invention. Furthermore, the terms and phrases used herein are not intended to be limiting but rather to provide an understandable description of the invention.

It is to be appreciated the systems, devices and methods presented herein may be used for surgical gas delivery, including insufflation, smoke evacuation, and/or recirculation in connection with suitable surgical devices, and in applicable surgical procedures. The present invention is particularly suited for minimizing the amount of equipment needed in a surgical operating room (operating theater), in that the subject systems are capable of performing multiple functions, and therefore also allow flexibility of surgical technique.

Figure 1B:
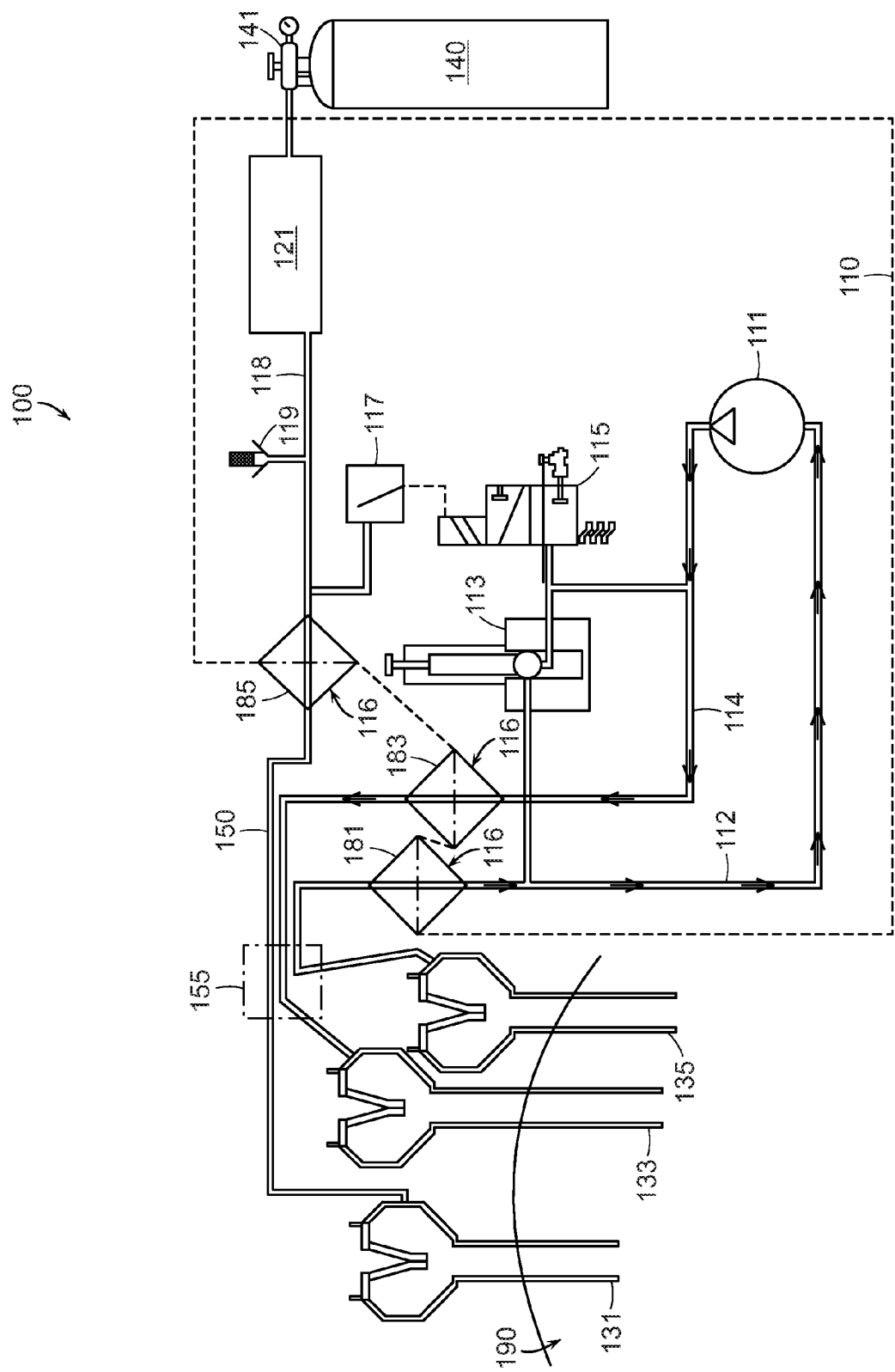
FIG. 1B is a schematic illustration of a multimodal surgical gas delivery system for laparoscopic surgical procedures in accordance with one aspect of the present invention.
Figure 2:
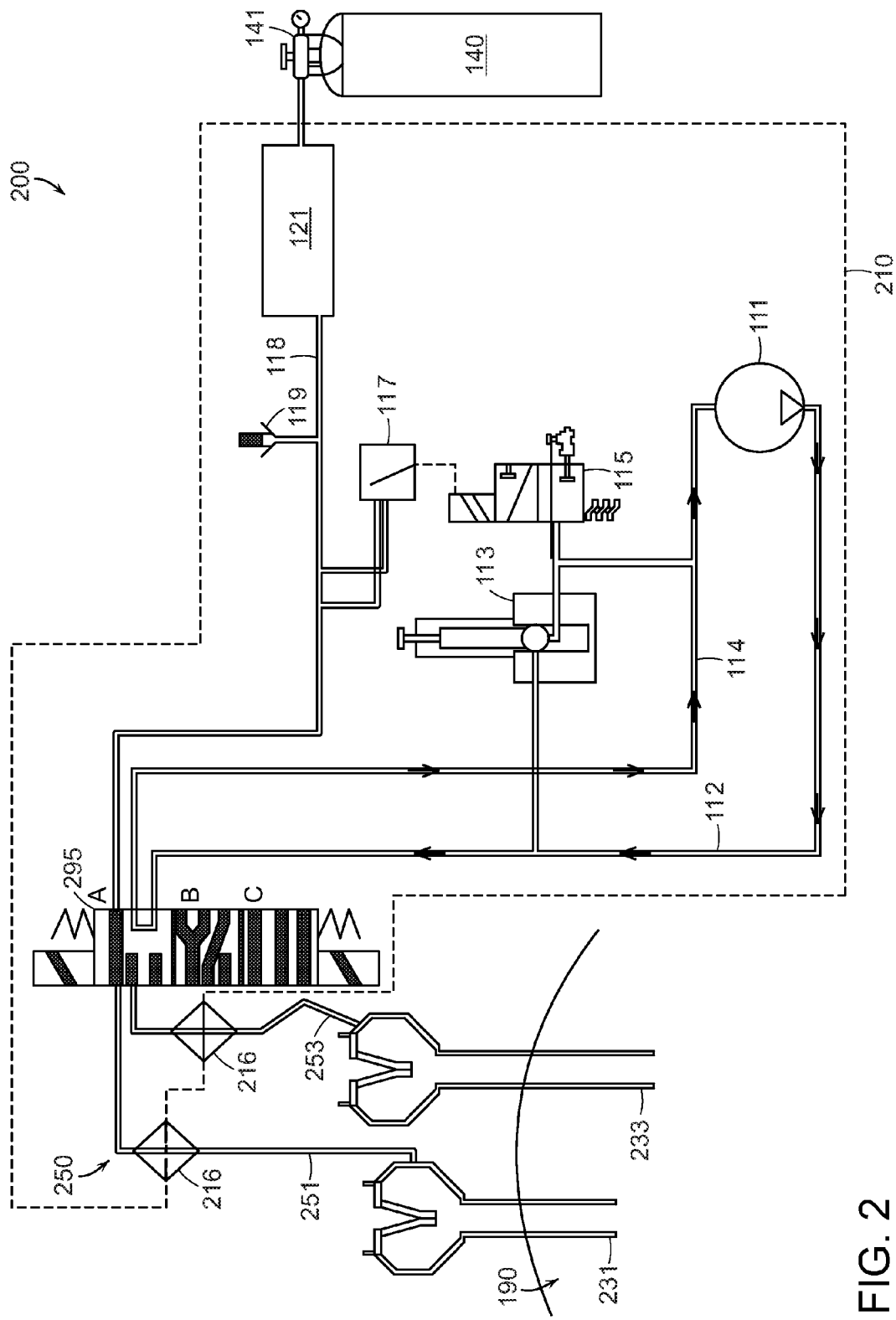
FIG. 2 is a schematic illustration of a multimodal surgical gas delivery system for laparoscopic surgical procedures in accordance with a further aspect of the present invention.
Figure 3:
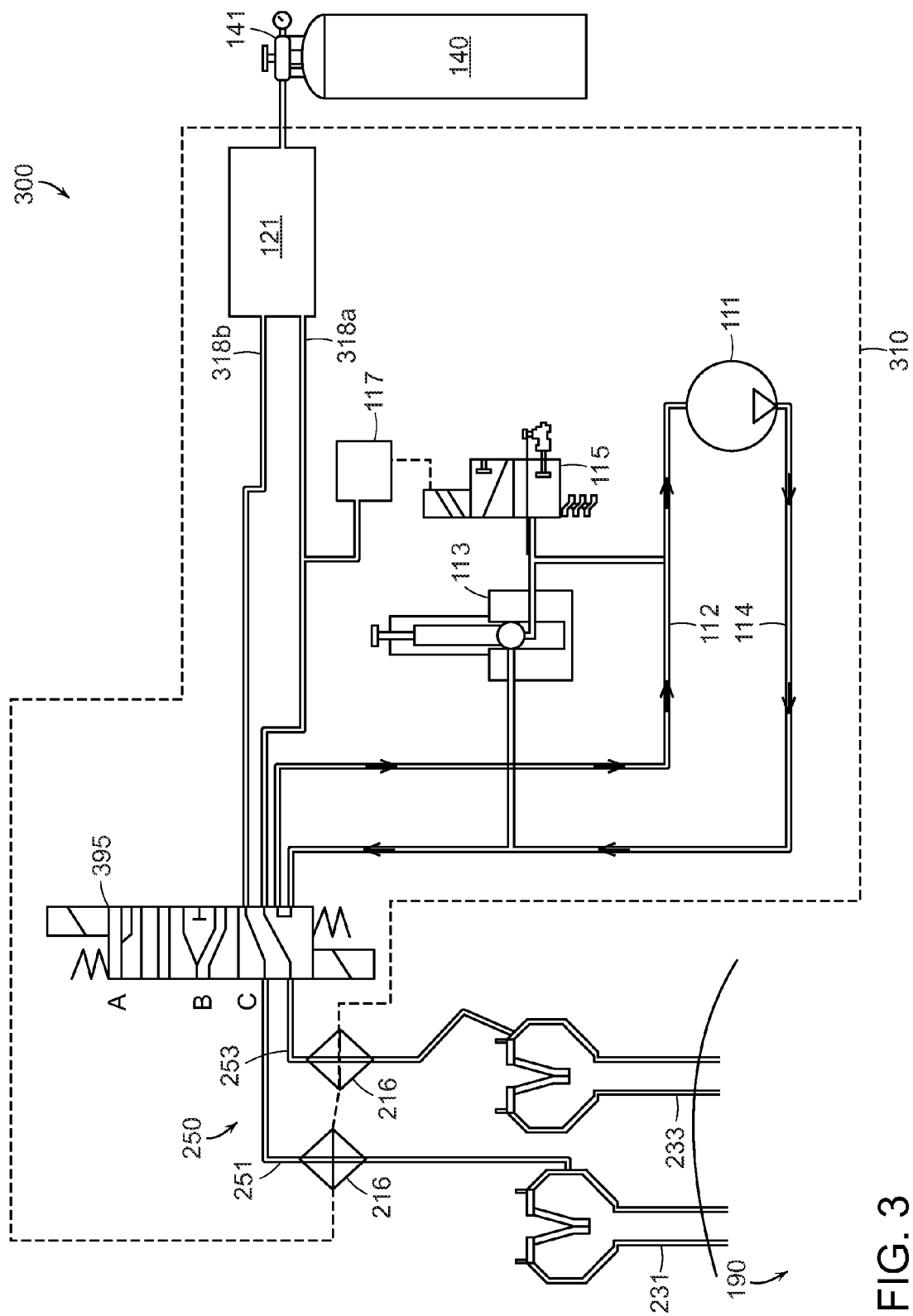
FIG. 3 is a schematic illustration of a multimodal surgical gas delivery system for laparoscopic surgical procedures in accordance with still a further aspect of the present invention.

FIGS. 1B, 2 and 3 illustrate different embodiments of systems of the present invention. The system 100 of FIG. 1B illustrates a multimodal system adapted and configured to operate in any selected mode using three surgical devices that are in fluid connection with a surgical cavity 190 (e.g. a patient's abdominal cavity). The system 200 of FIG. 2 and system 300 of FIG. 3 are each adapted and configured to operate in any selected mode using two surgical devices in fluid communication with a surgical cavity 190. In any case, it is conceived that additional surgical devices can be employed in parallel, for performing duplicative or still additional functions.

It is to be understood and appreciated, such surgical devices can be any desired device capable of permitting fluid communication, including but not limited to standard surgical access devices (e.g. trocars, cannulas), veress needles, and the like. It is conceived that the subject systems can alternatively or additionally be adapted and configured to interface with a main lumen of such access devices by mounting to the proximal end portion thereof, or alternatively by a fluid conduit placed through the lumen of the access device. Such an arrangement may be desirable in cases where a volumetric flow of fluid to be passed through the system exceeds a capacity of an insufflation port and/or stopcock on a standard surgical access device. Typically, surgical access devices are provided with a stopcock arranged in fluid communication with a space defined below a seal element to permit connection to an insufflator.

Systems described in U.S. Patent Publication No. 2007/0088275, as well as in U.S. Patent Application Ser. No.

61/104,448, filed Oct. 10, 2008, for example, provide pressurized gas to and remove depressurized gas from specialized surgical access devices, which penetrate into a surgical cavity, such as a patient's abdominal cavity. The access devices are adapted and configured to form a pressure barrier to inhibit losses of insufflation gas to the atmosphere. Gas from the abdomen interchanges with gas coming from the access device(s), a portion of which is collected and recycled through the system, and is re-pressurized, passing through one or more filters along the way. During this recycling process, smoke and/or other circulating debris, such as atomized fluids, are removed by the filters improving visibility within the surgical cavity, thus aiding in the surgical procedure.

Systems of the present invention utilize the inherent smoke and debris clearing capability of the systems configured for use with the aforementioned surgical access devices to perform additional functions with conventional access devices, including insufflation and smoke evacuation in which an exemplary embodiment that may be used with the system of the present invention is disclosed in U.S. patent application Ser. No. 12/587,584, filed Oct. 9, 2009 which is hereby incorporated by reference in its entirety.

As mentioned above, three illustrated embodiments are described herein. Each system of each embodiment may selectively provide one or more of the following modes of operation:

A first mode of operation for providing a pressurized insufflation fluid from an insufflation gas source into a surgical device for providing and maintaining sealable access to the body cavity in the surgical device. More specifically, a surgical device is adapted for introducing surgical instruments into a body cavity wherein the surgical device (e.g., a trocar) includes an outer tubular member having opposed proximal and distal end portions, the proximal end portion of the outer tubular member having a proximal housing associated therewith. Further provided is an inner tubular member having opposed proximal and distal end portions, the inner tubular member having a proximal flange at a proximal end thereof which is preferably seated within the proximal housing of the outer tubular member so as to define a plenum chamber within the proximal housing of the outer tubular member above the proximal flange of the inner tubular member. The plenum chamber is preferably in fluid communication with an annular nozzle configured to direct pressurized fluid in an axial direction from the plenum chamber into a central bore of the inner tubular member to provide a constant gaseous seal around a surgical instrument inserted through the central bore of the inner tubular member while simultaneously preventing a loss of pressurized fluid from the body cavity through the central bore of the inner tubular member. The plenum chamber is adapted and configured to receive pressurized fluid and conduct the pressurized fluid to the annular nozzle. Such a surgical device is disclosed in U.S. Pat. No. 7,413,559, filed Sep. 8, 2006 which is incorporated by reference in its entirety.

A second mode of operation for performing smoke evacuation in a filter element provided in the multimodal system from insufflation fluid caused to recycle through the multimodal system from the body cavity via a surgical device.

A third mode of operation for providing insufflation fluid from an insufflation gas source into the body cavity for creating and maintaining insufflation of the body cavity.

The first arrangement preferably enables smoke removal and insufflation using three conventional access devices. The second and third arrangements enable smoke removal and insufflation using only two conventional access devices.

It is to be appreciated each of the illustrated embodiments of FIGS. 1B, 2 and 3 include a computer-controlled control unit (110, 210 and 310) wherein each preferably includes a software algorithm, program or code residing on computer useable medium having control logic for enabling execution on a surgical system (100, 200 and 300) using a computer processor. The computer-controlled control unit (110, 210 and 310) typically includes memory storage configured to provide output from execution of the computer algorithm or program. FIG. 1A depicts an exemplary general-purpose computing system which may be used with the computer-controlled control unit (110, 210 and 310) as illustrated in the various embodiments (FIGS. 1B, 2 and 3) of present invention.

The computing system 10 of FIG. 1A generally comprises at least one processor 12, or processing unit or plurality of processors, memory 14, at least one input device 16 and at least one output device 18, coupled together via a bus or group of buses 11. In certain embodiments, input device 16 and output device 18 could be the same device. An interface 15 can also be provided for coupling the computing system 10 to one or more peripheral devices, for example interface 15 could be a PCI card or PC card. At least one storage device 14 which houses at least one database 17 can also be provided. The memory 14 can be any form of memory device, for example, volatile or non-volatile memory, solid state storage devices, magnetic devices, etc. The processor 12 could comprise more than one distinct processing device, for example to handle different functions within the processing system 10. Input device 16 receives input data 19 and can comprise, for example, a keyboard, a pointer device such as a pen-like device a mouse, a touch screen, or any other suitable device, such as a modem or wireless data adaptor, data acquisition card, etc. Input data 19 could come from different sources, for example keyboard instructions in conjunction with data received via a network. Output device 18 produces or generates output data 20 and can comprise, for example, a display device or monitor in which case output data 20 is visual. Output data 20 could be distinct and derived from different output devices, for example a visual display on a monitor in conjunction with data transmitted to a network. A user could view data output, or an interpretation of the data output, on, for example, a monitor or using a printer. The storage device 14 can be any form of data or information storage means, for example, volatile or non-volatile memory, solid state storage devices, magnetic devices, etc.

In use, the computing system 10 is adapted to allow data or information to be stored in and/or retrieved from, via wired or wireless communication means, at least one database 17. The interface 15 may allow wired and/or wireless communication between the processing unit 12 and peripheral components that may serve a specialized purpose. Preferably, the processor 12 receives instructions as input data 19 via input device 16 and can display processed results or other output to a user by utilizing output device 18. More than one input device 16 and/or output device 18 can be provided. It should be appreciated that the computing system 10 may be any form, but is preferably provided integral with each system 100, 200 and 300 of the illustrated embodiments herein.

It is to be appreciated that the computing system 10 may be a part of a networked communications system. Computing system 10 could connect to a network, for example the Internet or a WAN. Input data 19 and output data 20 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the computing system 10 illustrated in FIG. 1A may operate in a networked environment using logical connections to one or more remote computers. The remote computer may be a personal computer, a server, a router, a network PC, a tablet device, a peer device, or other common network node, and typically includes many or all of the elements described above.

FIG. 1A is intended to provide a brief, general description of an illustrative and/or suitable exemplary environment in which embodiments of the below described present invention may used with. FIG. 1A is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

As illustrated in FIG. 1B, a multimodal surgical gas delivery system 100 preferably includes a fluid pump 111 adapted and configured to circulate insufflation fluid through the system 100. A supply conduit 114 is in fluid communication with an output of the fluid pump 111 and is configured and adapted for delivering pressurized insufflation fluid to an output port 183 of the control unit 110. A return conduit 112 is in fluid communication with an input of the fluid pump 111 for delivering insufflation fluid to the fluid pump 111, and is configured and adapted for returning insufflation fluid to an input port 181 of the control unit 110. It is to be understood and appreciated the control unit 110 includes aforesaid computing system 10 which is preferably coupled to the components of system 100 for facilitating the selective modes of operation as described above.

An adjustable back-pressure control valve 113 is provided in fluid communication with the supply conduit 114 and the return conduit 112, and is adapted and configured to respond to a supply conduit pressure exceeding a set pressure, by opening and directing fluid from the supply conduit 114 to the return conduit 112. The back-pressure control valve 113 can be a mechanical valve, such as a resiliently-biased valve.

Alternatively, the back-pressure control valve 113 can be an electro-mechanical valve, responding to a high pressure signal from one or more pressure sensors (e.g. 117) within the system 100.

An insufflation subunit 121 is provided and is adapted and configured to receive a supply of insufflation gas (e.g. carbon dioxide) from a source 140 (e.g. a local tank or central distribution system), which may also pass through a pressure regulator 141 prior to entering the system 100. The insufflation subunit 121 is connected through an insufflation conduit 118 for delivering insufflation gas to the rest of the system 100 from the insufflation subunit 121, and includes a pressure sensor (not illustrated separately) adapted and configured to sense pressure of a surgical cavity 190 through the insufflation conduit, and an insufflation control (not illustrated separately), for controlling (as by stopping and starting) addition of insufflation fluid into the system 100, from the source 140.

Further, the system 100, or any system described herein, is controlled by a user through a control panel, such as one provided on or otherwise in connection with the control unit 110. Such control panel is preferably adapted and configured to permit a user to select a mode for the multimodal surgical gas delivery system, such as by way of a switch, touch screen or other user interface, such as a graphical user interface (GUI) that permits flexibility of the unit 110, while reducing clutter and/or confusion due to excess controls, permitting only selection from a predetermined set of appropriate parameters in any given mode. It is to be understood and appreciated the control panel may be provided integral with the system 100 or remotely located therefrom using known means of data communication.

After selecting a mode as described above (including, but not limited to insufflation only, smoke evacuation only, combined smoke evacuation and insufflation, recirculation only, or combined recirculation and smoke evacuation, for example), parameters that may be adjustable include, for example, flow rate (e.g. liters/minute), pressure (e.g. in mmHg), and conditioning parameters (e.g., temperature, humidity), and the like. As used herein, such "recirculation" mode, alone or combined with other modes, is one that is suitable for providing sufficient pressures and flow rates to drive surgical access devices such as those described in U.S. Patent Publication No. 2007/0088275, as well as in U.S. Patent Application Ser. No. 61/104,448, filed Oct. 10, 2008, and/or those described in U.S. Pat. Nos. 7,182,752, 7,285, 112, 7,413,559 or 7,338,473, for example, each of which is incorporated by reference in its entirety.

A conduit set or tube set 150 is also preferably provided, and is adapted and configured to connect at one end to the supply 114, return 112 and insufflation 118 conduits, and at the opposing end to a plurality of surgical devices 131, 133, 135, provided in fluid communication with the surgical cavity 190. The configuration of the tube set 150 can vary, depending on the desired implementation, as mentioned above. In the case of the system 100 of FIG. 1B, the tube set 150 preferably has a unitary, multi-lumen connection to input 181, output 183 and insufflation 185 ports, and separate connections to individual surgical devices 131, 133, 135.

In one preferred aspect, the tube set 150 has a compound, multi-lumen tube, beginning at the connections to the ports 181, 183, 185 to the control unit 110 for a predetermined distance from the control unit 110, generally until about the distance between the control unit 110 and an operating table, at which point a furcation 155 yields multiple separate tubes. In the case of the system 100 of FIG. 1B, three separate tubes, separately lead to each of the surgical devices 131, 133, 135, which may be surgical access devices (e.g., cannulas, trocars) with insufflation capability, or other instruments, such one or more veress needles. The surgical devices are thus individually connected to one of the supply 114, return 112 and insufflation 118 conduits, and therefore respectively facilitates that function. That is, the surgical devices 131, 133, 135 facilitate insufflation into and sensing of, supply filtered insufflation gas to, or remove contaminated gas from the abdominal cavity 190.

As set forth above, in one preferred aspect, the separate distal tube portions of the tube set 150 are connected by way of a conventional fitting, such as a luer-lock fitting on a conventional surgical device. The precise configuration of the tube set 150 can vary depending on the desired configuration. Moreover, as described for example, in U.S. patent application Ser. No. 11/960,701, filed Dec. 20, 2007; U.S. 61/104, 448, filed Oct. 10, 2008; and U.S. 61/195,898, filed Oct. 10, 2008, a unitary filter element can be provided to which the tube set 150 is connected. In such an arrangement, the filter(s) 116 is (are) arranged between the tube set 150 and the supply 114, return, 112 or insufflation 118 conduits, and is (are)

provided with integral input 181, output 183 and insufflation 185 ports, which can be a unitary, multi-lumen connection, for example.

A filter 116 that is suitable for one application or function, may be suitable for use in another application or function. For example, a filter suitable for use in a recirculation function with specialized surgical access devices, such as Air Seal™ surgical cannulas, available from SurgiQuest, Inc., Orange, Conn. USA, as described in whole or in part in U.S. Pub. No. 2007/0088275 and U.S. 61/104,448, filed Oct. 10, 2008, for example, may be suitable for use in smoke evacuation and insufflation functions using conventional surgical access devices, requiring only a different, particular tube set 150. The above-mentioned SurgiQuest Air Seal™ surgical cannulas utilize relatively large flow rates compared to flow rates needed for smoke evacuation and/or insufflation, and therefore a filter suitable for large flow rates will likely be suitable for smaller flow rates.

Alternatively, a specially configured filter can be provided, with dimensions and other parameters tailored to flow rates of different functions. Moreover, the tube set 150 and filter 116 can be mutually configured as a set for a particular application and provided as a kit, and permanently connected, if desired.

If so desired, systems in accordance with the invention can be provided with capability to automatically identify consumables (e.g., filters and/or tube sets) used in connection with the system, such as by a radio-frequency identification (RFID) transponder, bar code, or other data-carrying element provided thereon. In such an arrangement, the system (e.g. 100) identifies the consumable and switches to the appropriate mode (e.g., recirculation, smoke evacuation, etc.).

Certain suitable filters and tube sets are set forth in U.S. patent application Ser. No. 12/577,188, filed Oct. 11, 2009, which is incorporated by reference herein in its entirety. In addition, further embodiments of filter assemblies 1000, 2000 are appended hereto in FIGS. 4(A)-4(X) and 5(A)-5(T), respectively. The filter embodiments of FIGS. 3 and 4 perform similar functions to those in U.S. Ser. No. 12/577,188, but contain additional refinements and features.

Figure 4A:
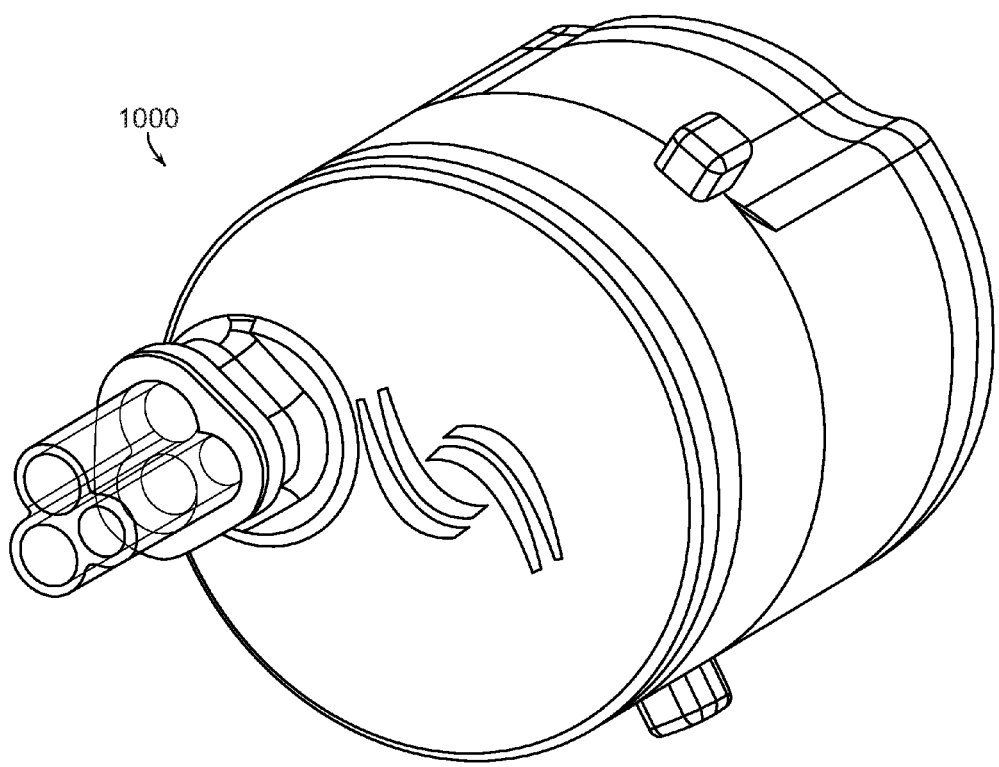
FIGS. 4(A)-4(X) illustrate various view of a filter assembly used in conjunction with the system of surgical gas delivery system for laparoscopic surgical procedures in accordance the present invention.
Figure 4B:
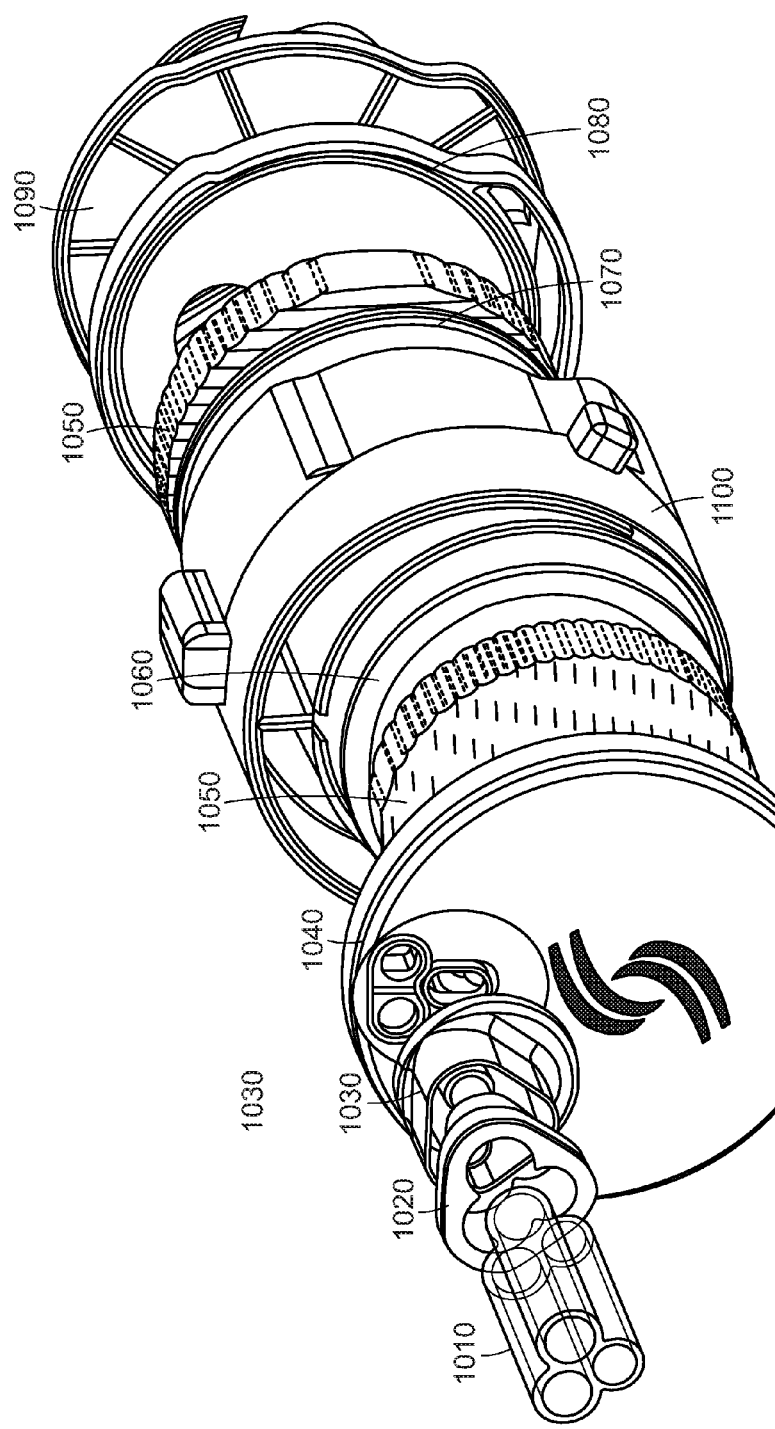
Figure 4C:
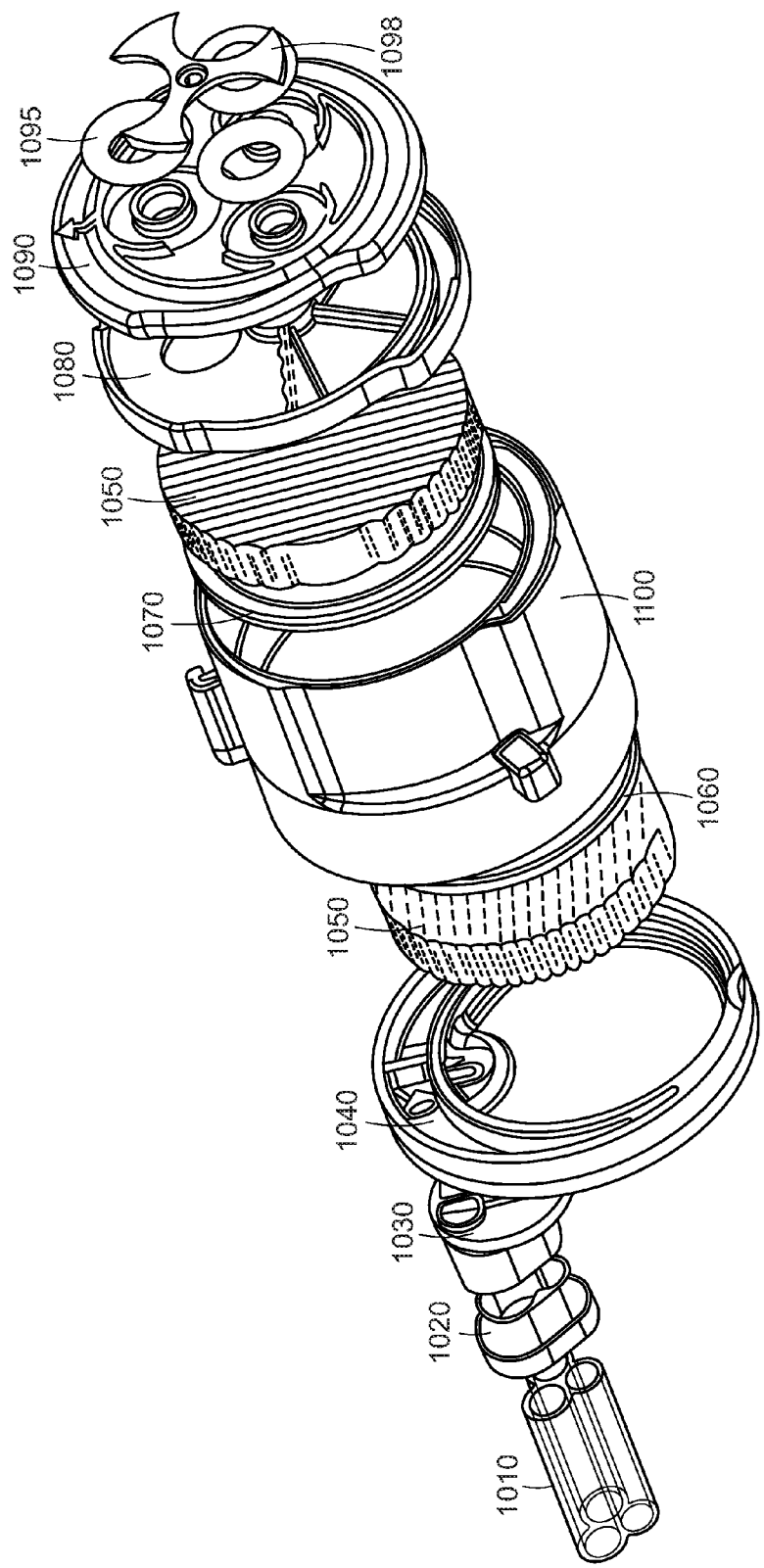
Figure 4D:
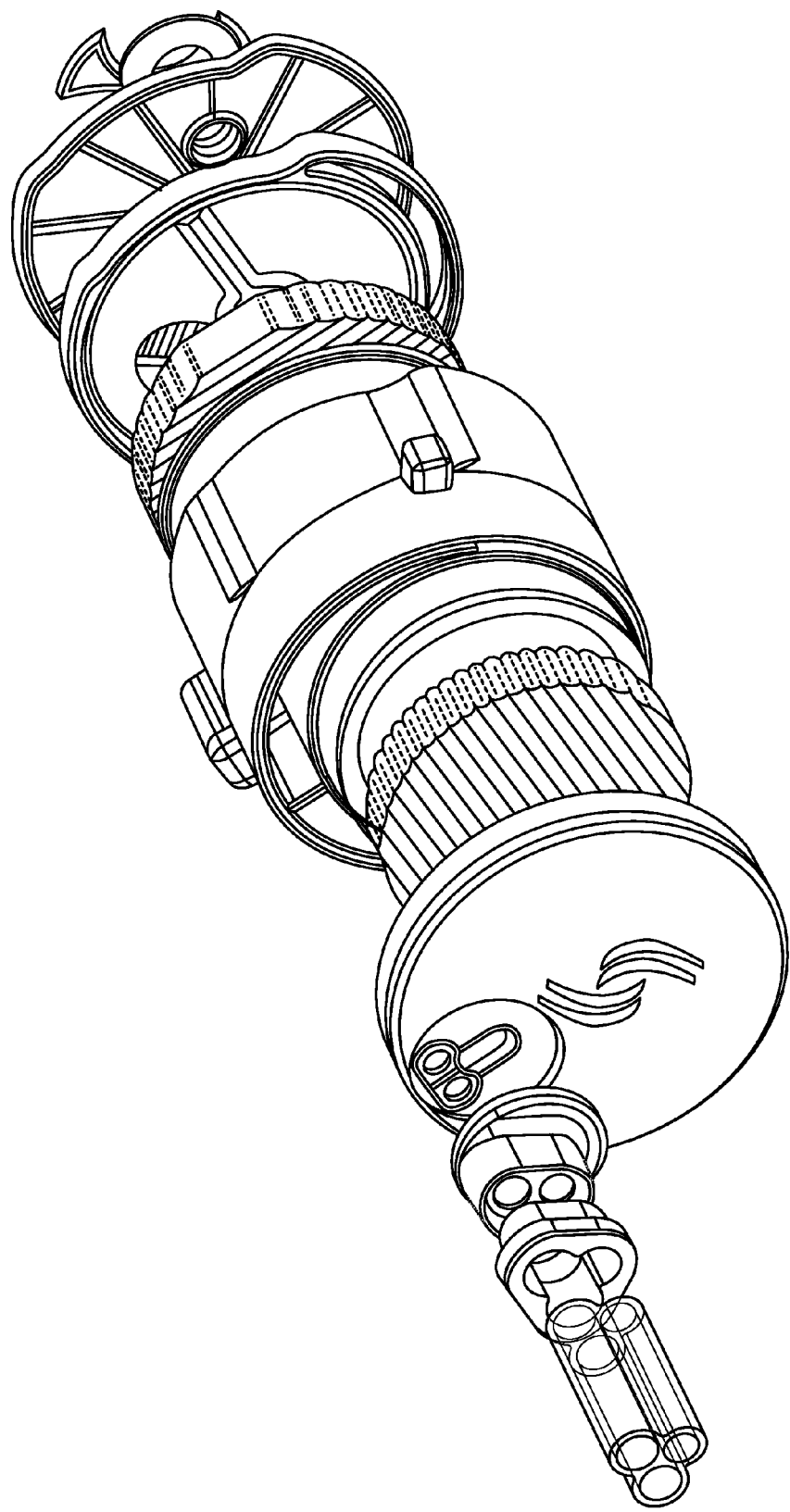
Figure 4E:
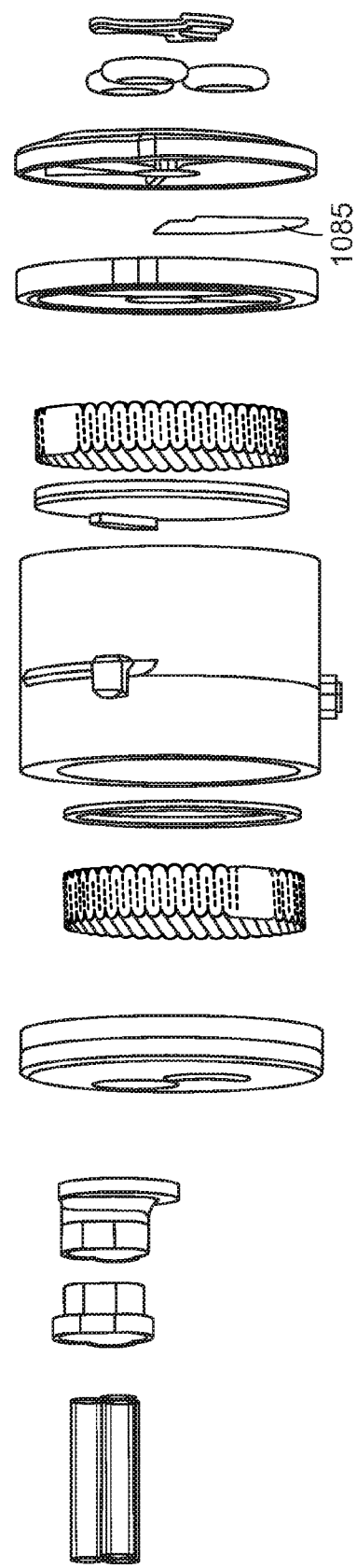
Figure 4F:
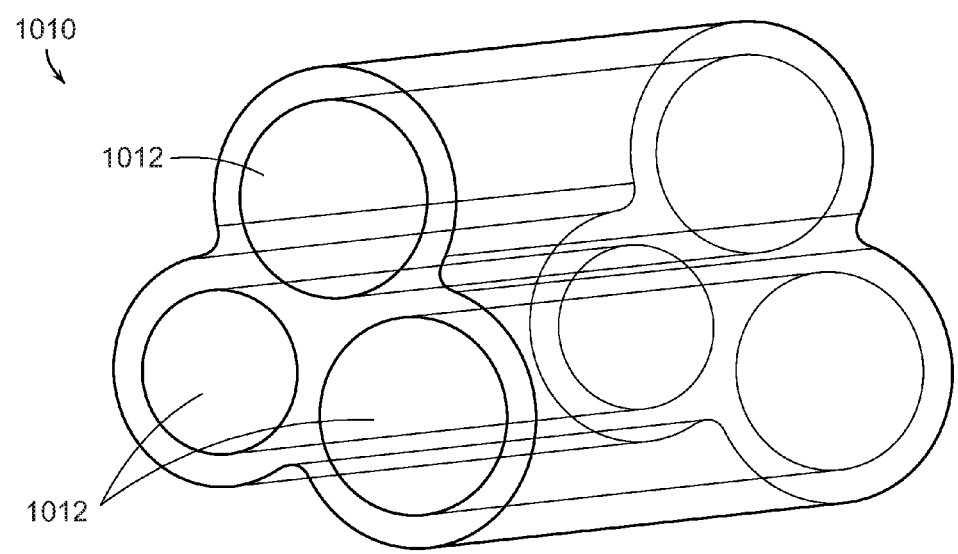
Figure 4H:
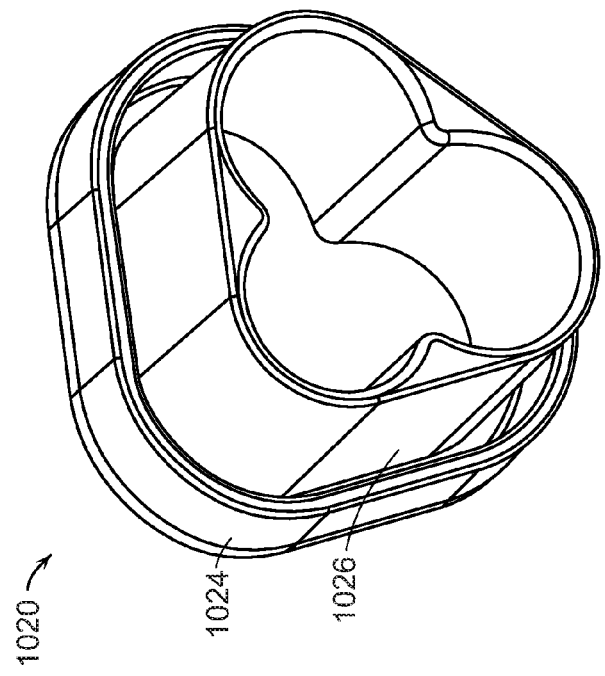
Figure 4G:
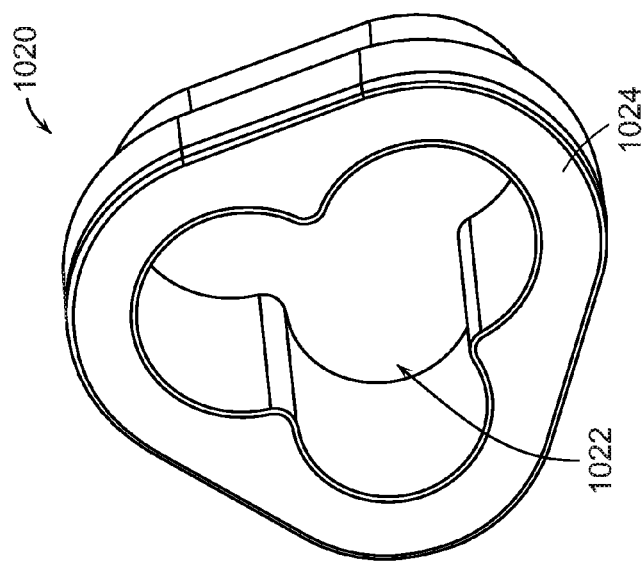
Figure 4J:
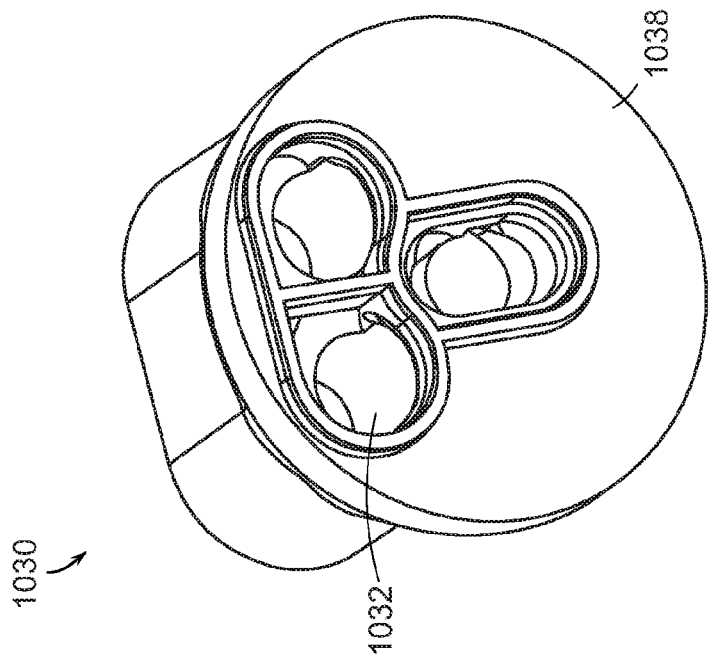
Figure 4I:
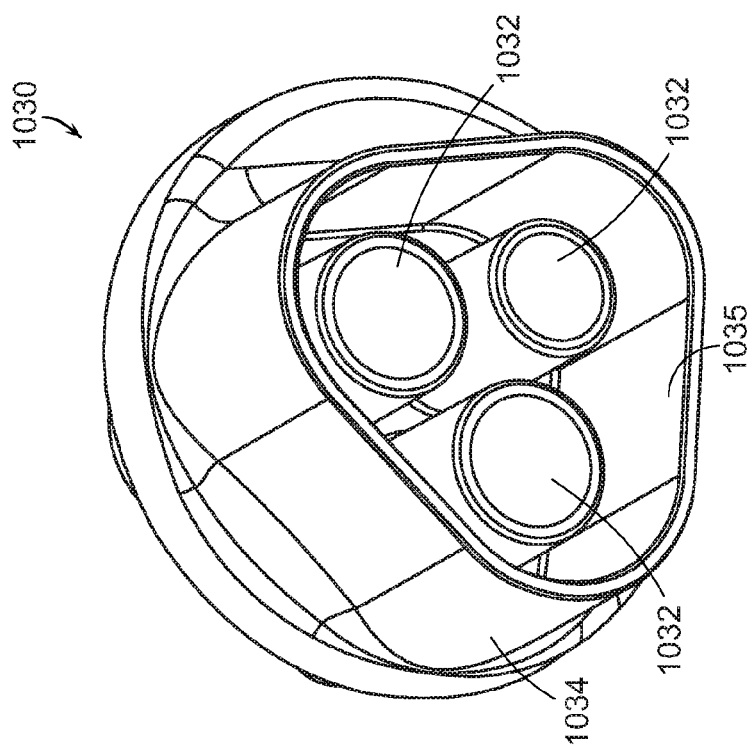
Figure 4L:
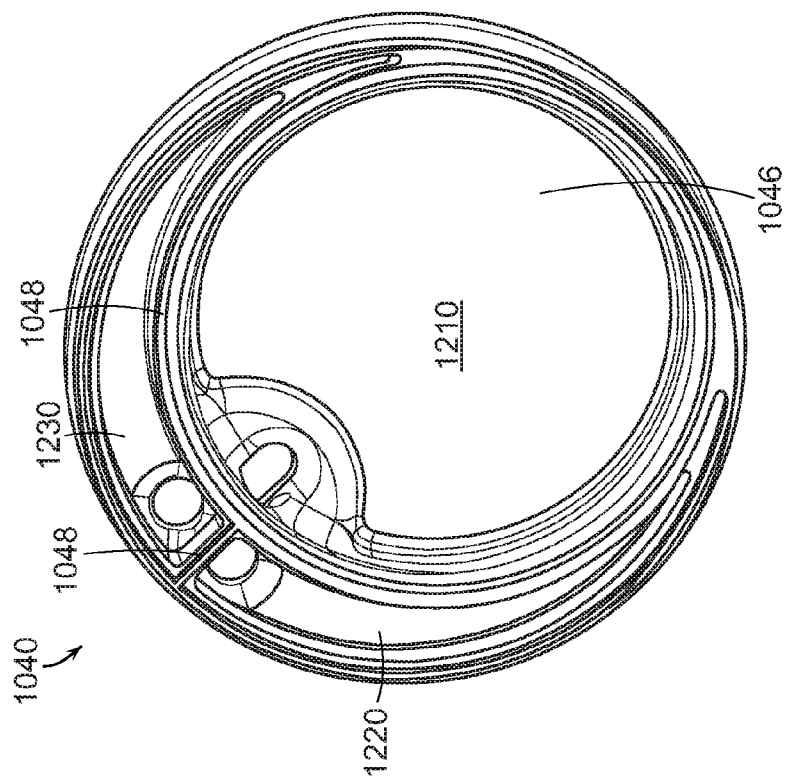
Figure 4K:
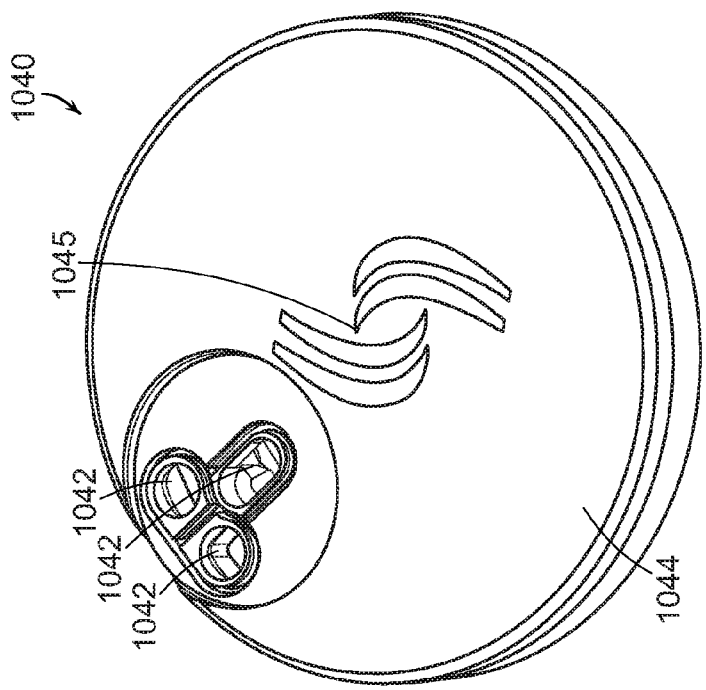
Figure 4N:
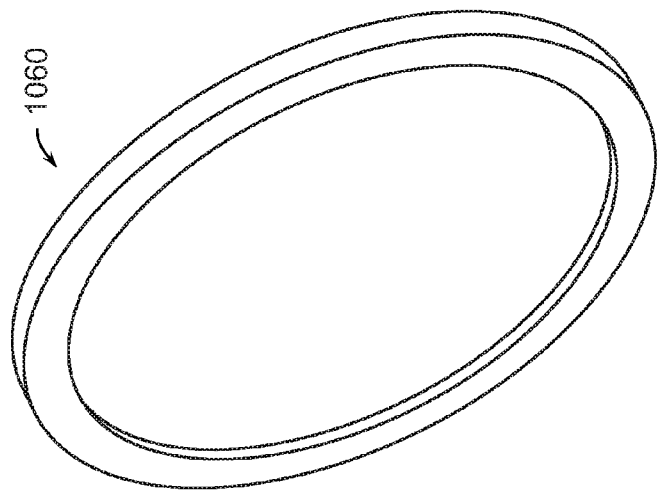
Figure 4M:
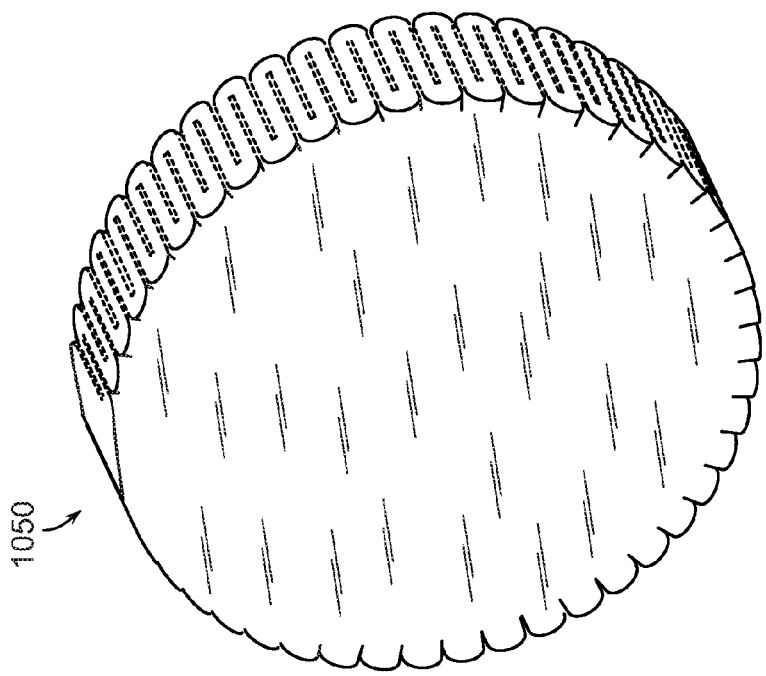

A first embodiment 1000 of filter is presented in FIGS. 4(A)-4(X). Filter 1000 includes a compression fitting 1020 received by an inlet or input manifold 1030 that cooperate to hold a tube set 1010 in place (FIGS. 4(B), 4(C)). Only a terminal portion of tubeset 1010 is pictured, including fluid flow passages 1012 (FIG. 4(F)), each of which can perform a separate function (e.g., delivery of insufflation gas, smoke evacuation and recirculation). Compression fitting 1020 (FIGS. 4(G), 4(H)) includes a body 1024 having a compression portion 1026 integrally formed therewith and defining an opening 1022 for receiving tubeset 1010. Manifold 1030 (FIGS. 4(I), 4(J)) includes a first portion 1034 for receiving tubeset 1010 with compression fitting 1020 mounted thereon. Compression of tubeset 1010 is achieved by an interference fit created by interference of tubeset 1010, fitting 1020 and the interior space 1035 of manifold 1030. Manifold 1030 defines three fluid passages 1032 therethrough from the inlet side depicted in FIG. 4(I) to outlet or reverse side 1038 depicted in FIG. 4(J). An inlet cover plate 1040 (FIGS. 4(K), 4(L)) is provided defining a plurality of fluid flow passages 1042 therethrough. Outwardly facing surface 1044 of cover plate 1040 may include indicia 1045 or the like. Inwardly facing surface 1046 is divided into three flow areas or plena (1210, 1220, 1230). Plena 1210, 1220, 1230 represent three individual fluid flow circuits that traverse filter 1000 from inlet to outlet. Pleated filter elements 1050 (FIG. 4(M)) and filter element 1085 (FIG. 4(E)) are provided for filtering fluid flowing through each of the plena 1210, 1220 and 1230. An o-ring 1260 (FIG. 4(N)), spacer or other suitable sealing element is provided for placement between filter element 1250 and housing 1100 when assembled.

Figure 4P:
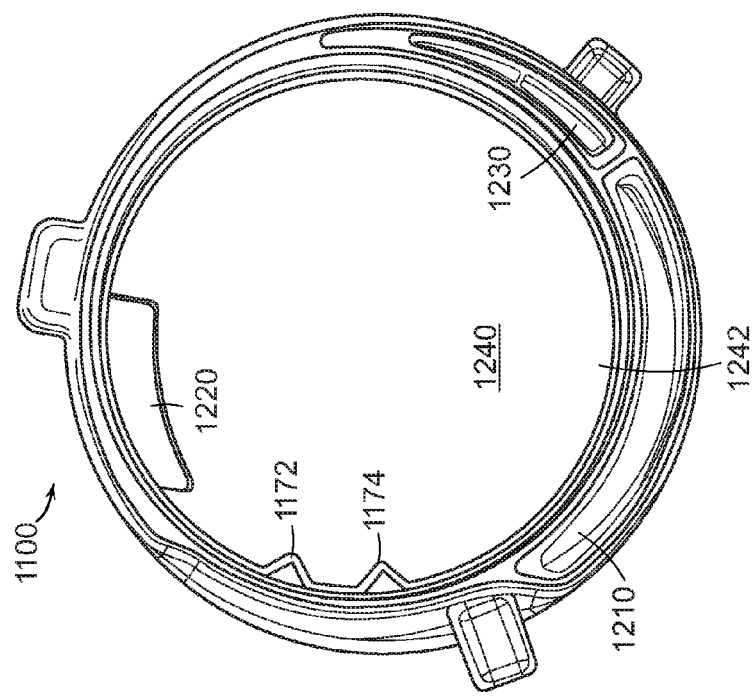
Figure 4O:
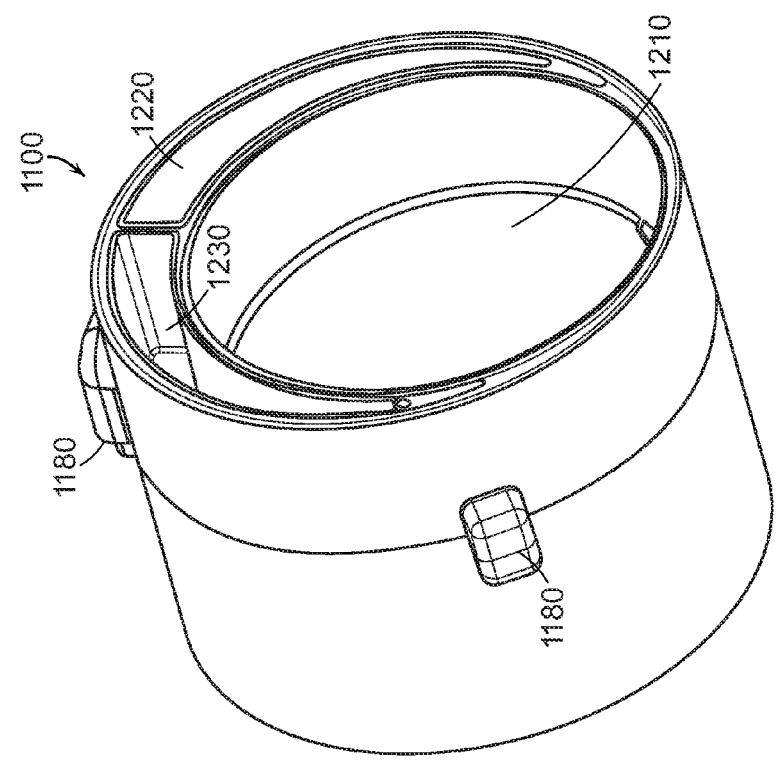
Figure 4Q:
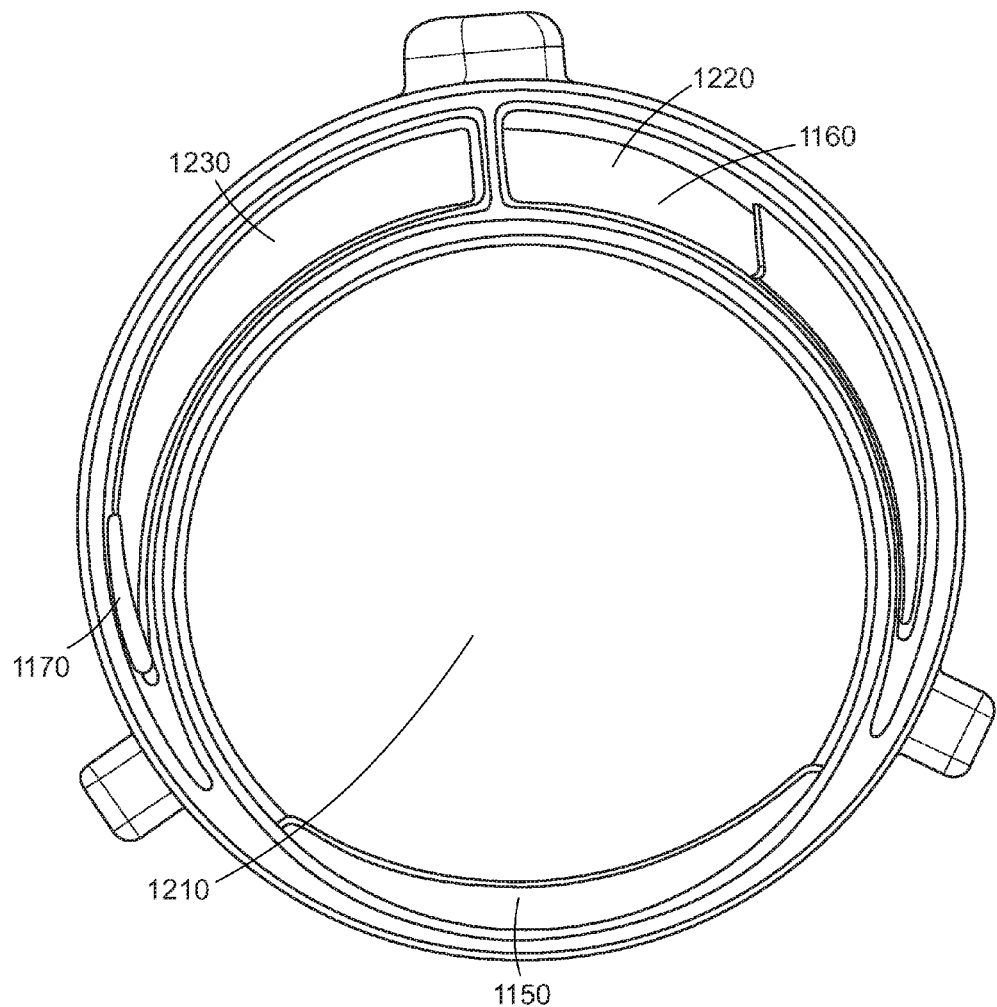
Figure 4S:
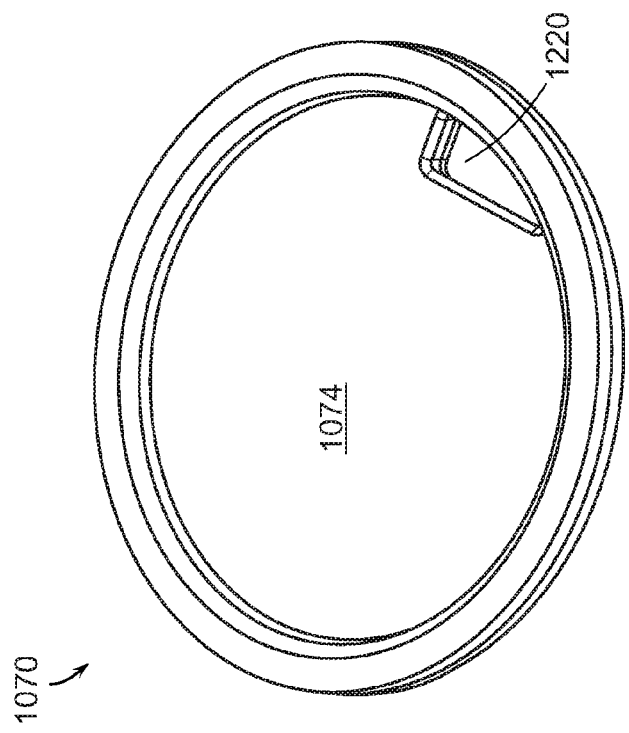
Figure 4R:
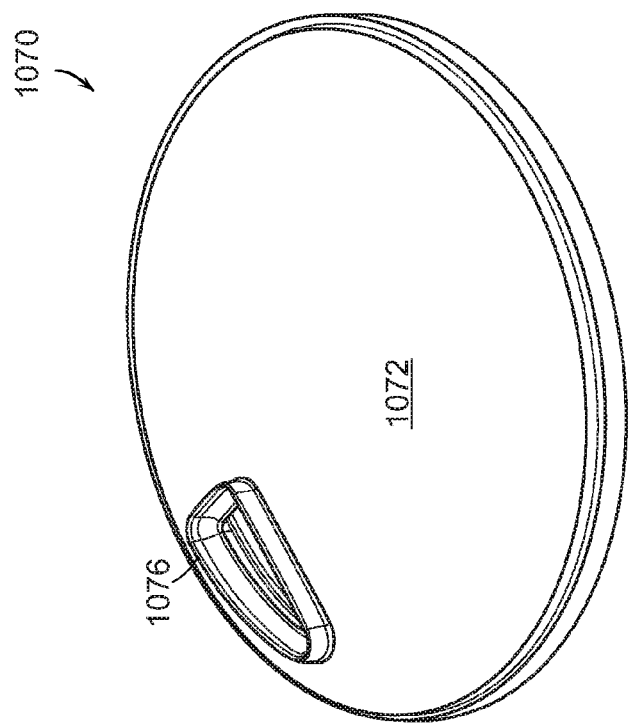

Filter housing 1100 (FIGS. 4(O), 4(P), 4(Q)) is configured to receive the other portions of filter assembly 1000 and to define passages for plena 1210, 1220, 1230. For example, as most clearly shown in FIG. 4(Q), an opening 1150 is defined proximate the bottom of housing 1100 to permit fluid to flow through plenum 1210, opening 1160 is provided to permit fluid to flow through plenum 1220, and opening 1170 is provided to permit fluid to flow through plenum 1230. Filter housing 1100 is preferably transparent, and includes integrally formed prisms 1172, 1174 for sensing rise of liquid level thereto when a reservoir 1240 (FIG. 4(P)) defined by cooperation of housing 1100 and reservoir backing plate 1070. Liquid entrained in gas being recirculated from the pneumoperitoneum collects in the reservoir 1240 and fills from the bottom 1242 thereof to a first setpoint level defined by the first prism 1172, and a second setpoint level defined by second prism 1174. The lead lines to each prism 1172, 1174 in FIG. 4P correlate approximately with the fluid level when the setpoint is achieved. The outer surface of housing 1100 proximate the location of the prisms 1172, 1174 is in optical communication with a sensor in the insufflation unit or other optical sensor that is adapted and configured to detect a change in the index of refraction in the region of the prism. One disclosed embodiment of a combined insufflation/recirculation/smoke evacuation system is included herewith as an Appendix from which dates have been redacted. Discussion of prisms 1172, 1174 and their function is described in further detail therein at section 5.6.8.1.1. If housing 1100 is provided as an opaque or coated unit, prisms are provided in a transparent form in accordance with their desired function. Reservoir backing plate 1070 (FIG. 4(R), FIG. 4(S)) includes a reservoir facing surface 1072 and a second surface 1074. Flow passage 1220 is provided therethrough by way of an opening surrounded by a raised boss 1076, which helps prevent fluid in the reservoir 1240 from splashing through the opening.

Figure 4U:
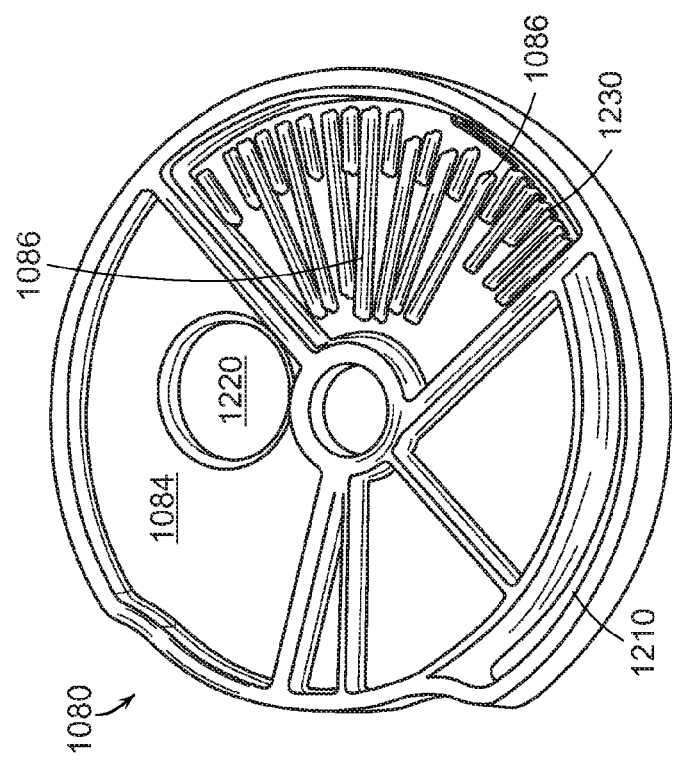
Figure 4T:
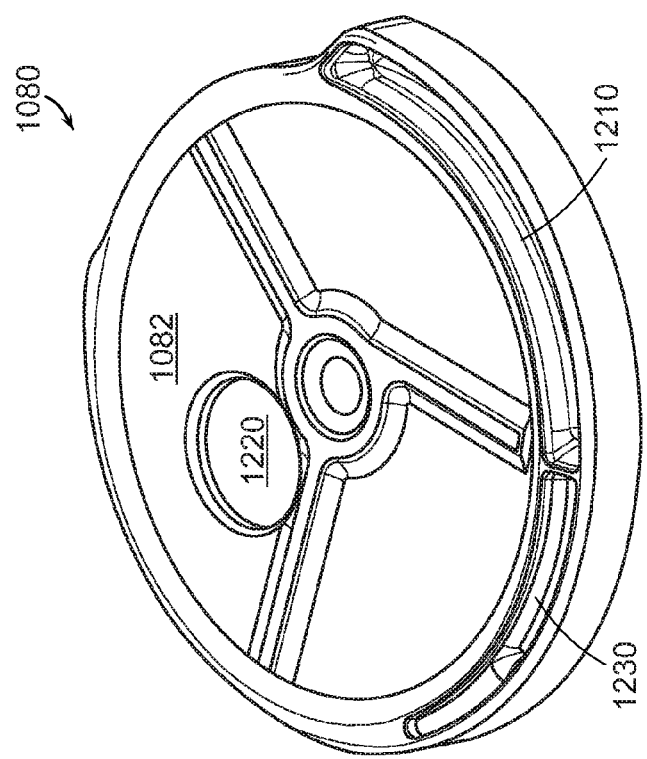
Figure 4W:
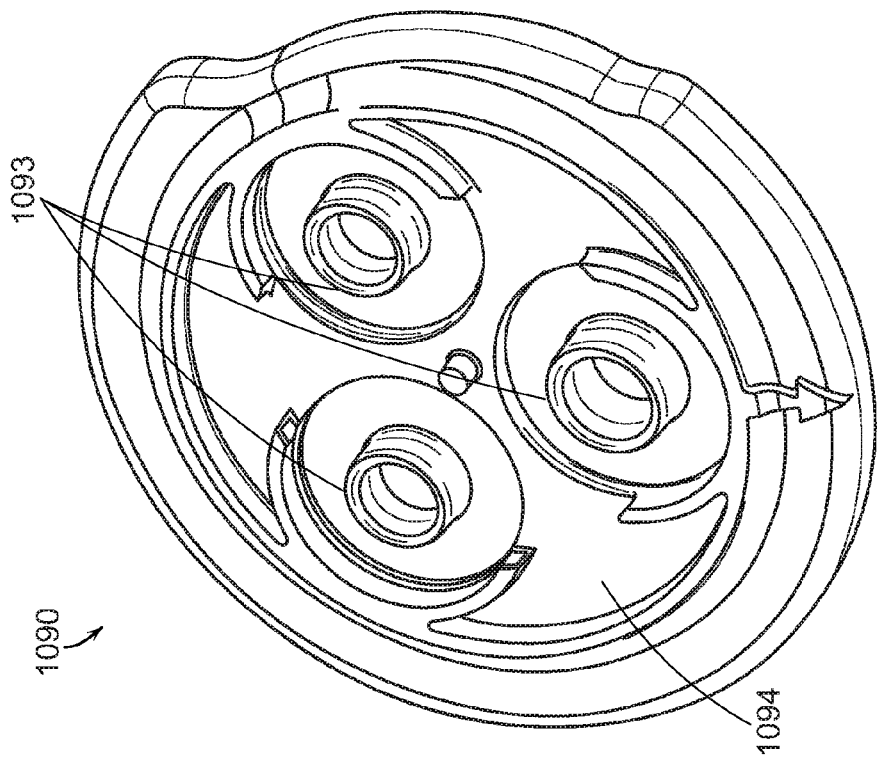
Figure 4V:
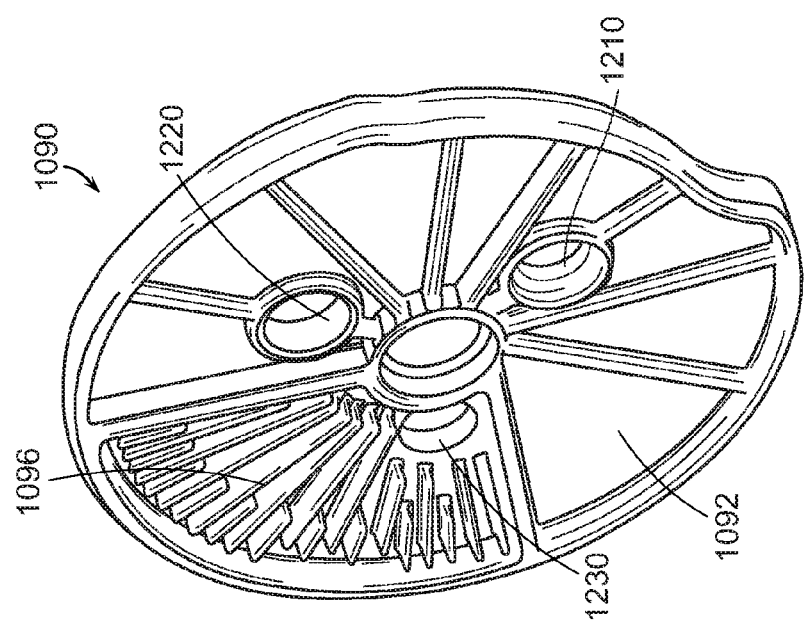

Diverter plate 1080 is illustrated in FIGS. 4(T) and 4(U). Surface 1082 faces the flow and surface 1084 faces end cap 1090 (FIGS. 4(V), 4W). End cap includes a first face 1092 and an outer face 1094 Passages are provided through plates 1080, 1090 to maintain fluid continuity for flow passages/plena 1210, 1220, 1230. Diverter fins 1086, 1096 are provided on plates 1080, 1090 for holding filter media 1085 in place. Bosses 1093 are provided for receiving O-rings (preferably made from silicone) also held in place by retainer 1098 (FIG. 4(X)). The various components of filters 1000, 2000 can be assembled using any suitable means, including but not limited to adhesive, ultrasonic welding and the like.

Figure 5A:
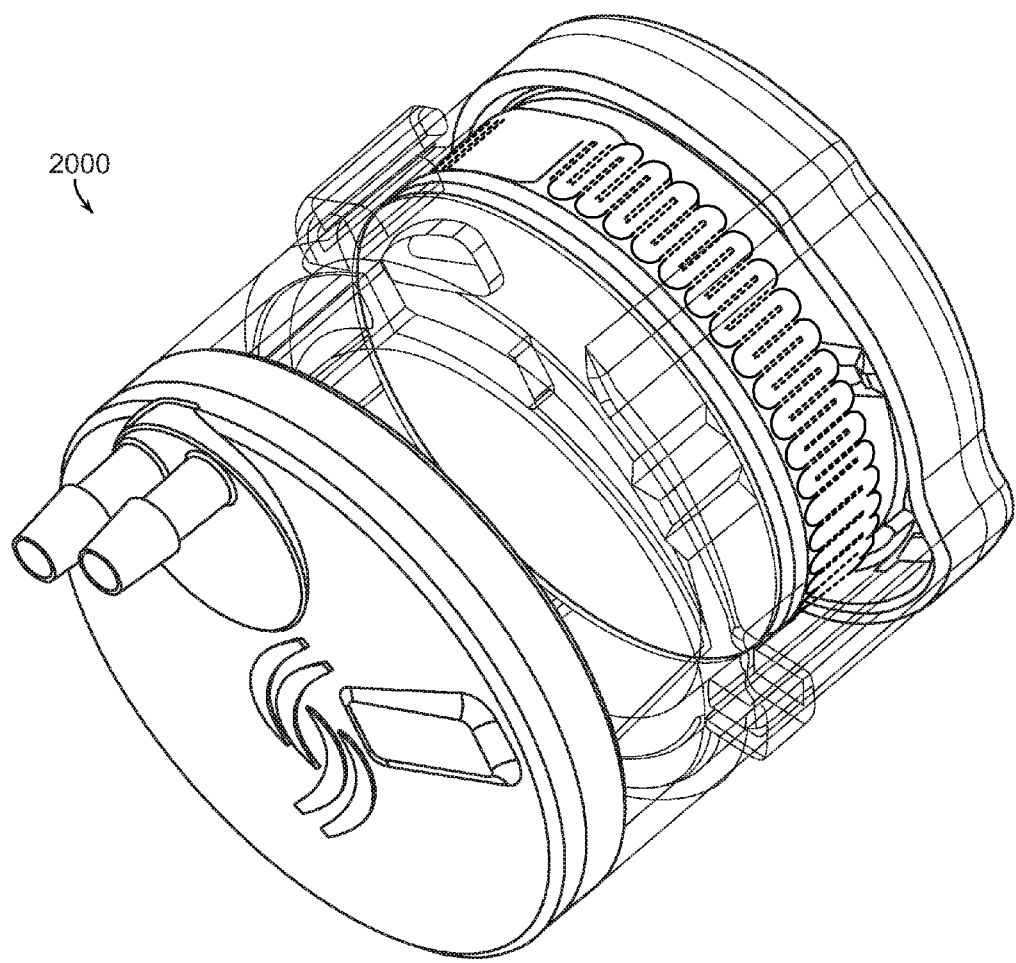
FIGS. 5(A)-5(T) illustrate various view of another illustrated embodiment of a filter assembly used in conjunction with the system of surgical gas delivery system for laparoscopic surgical procedures in accordance the present invention.
Figure 5B:
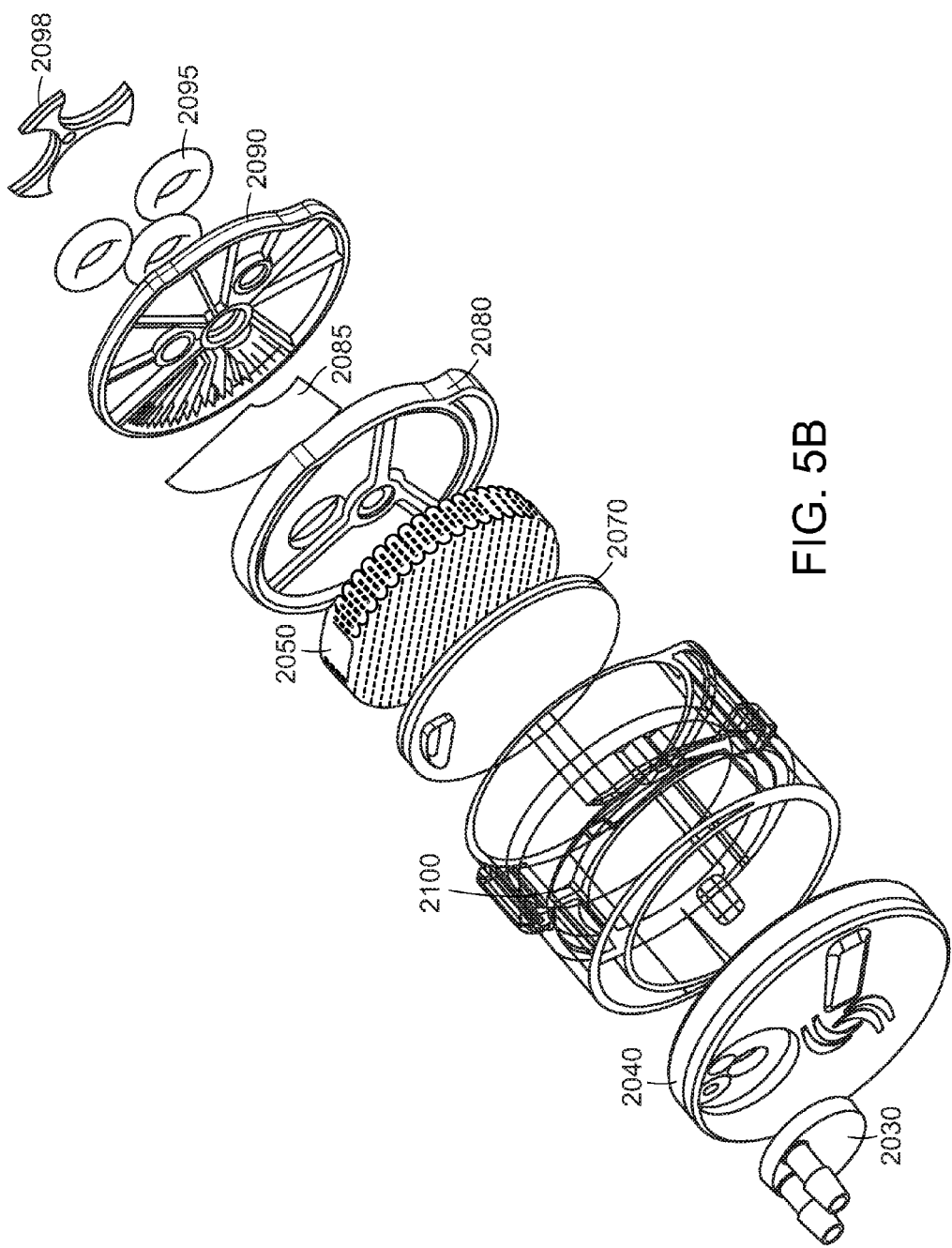
Figure 5C:
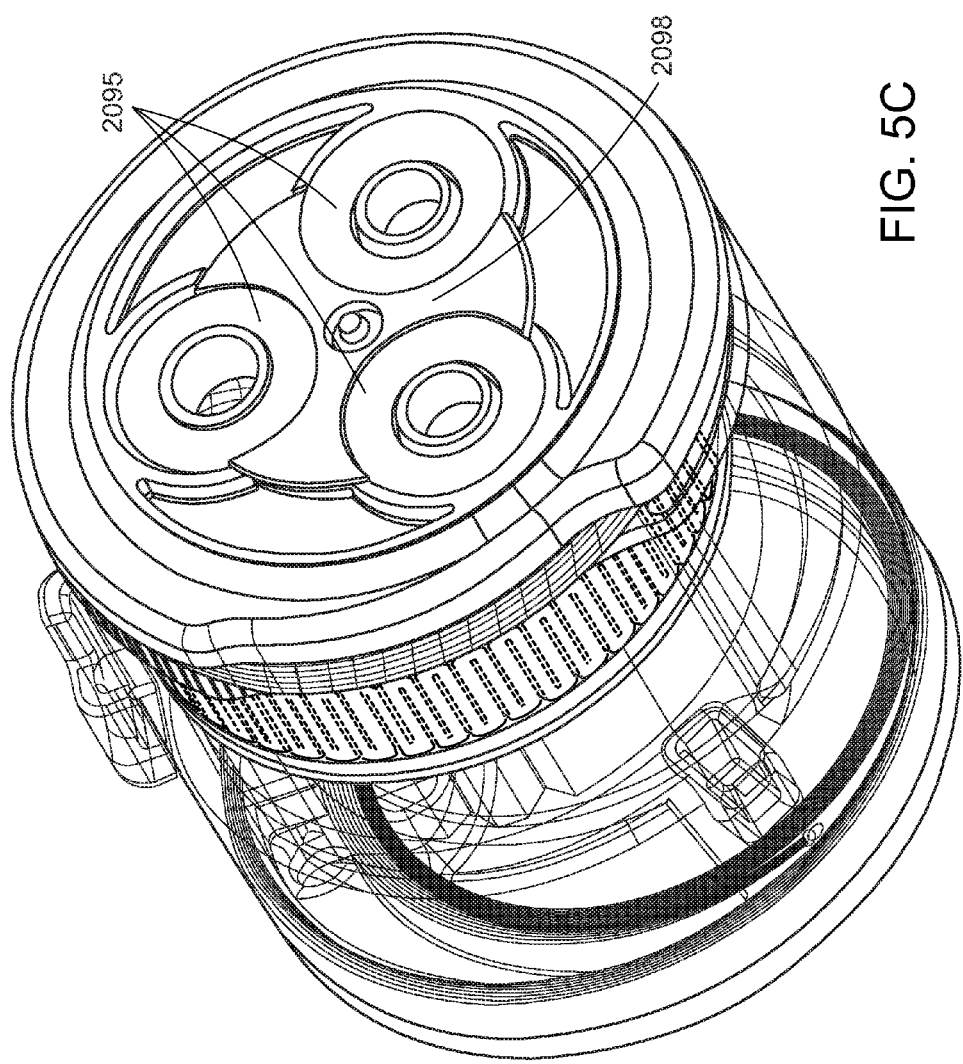
Figure 5D:
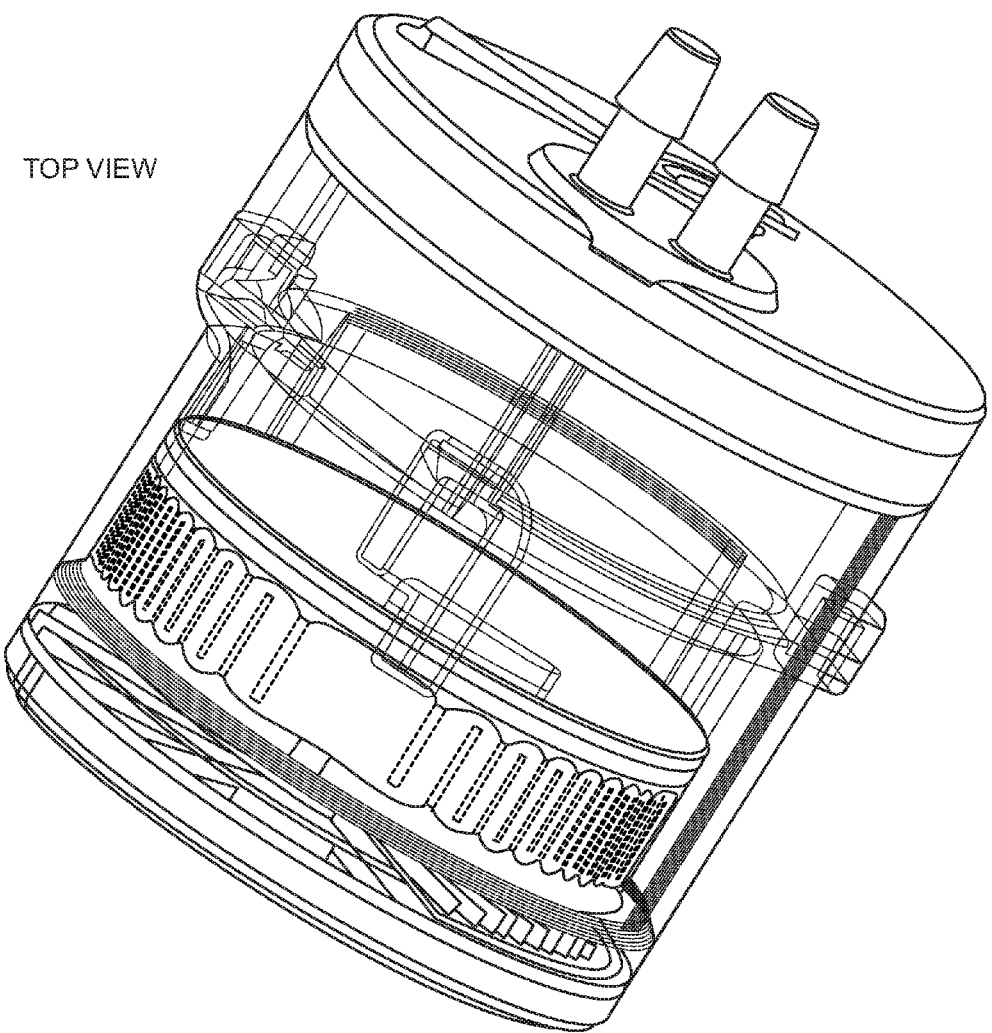
Figure 5E:
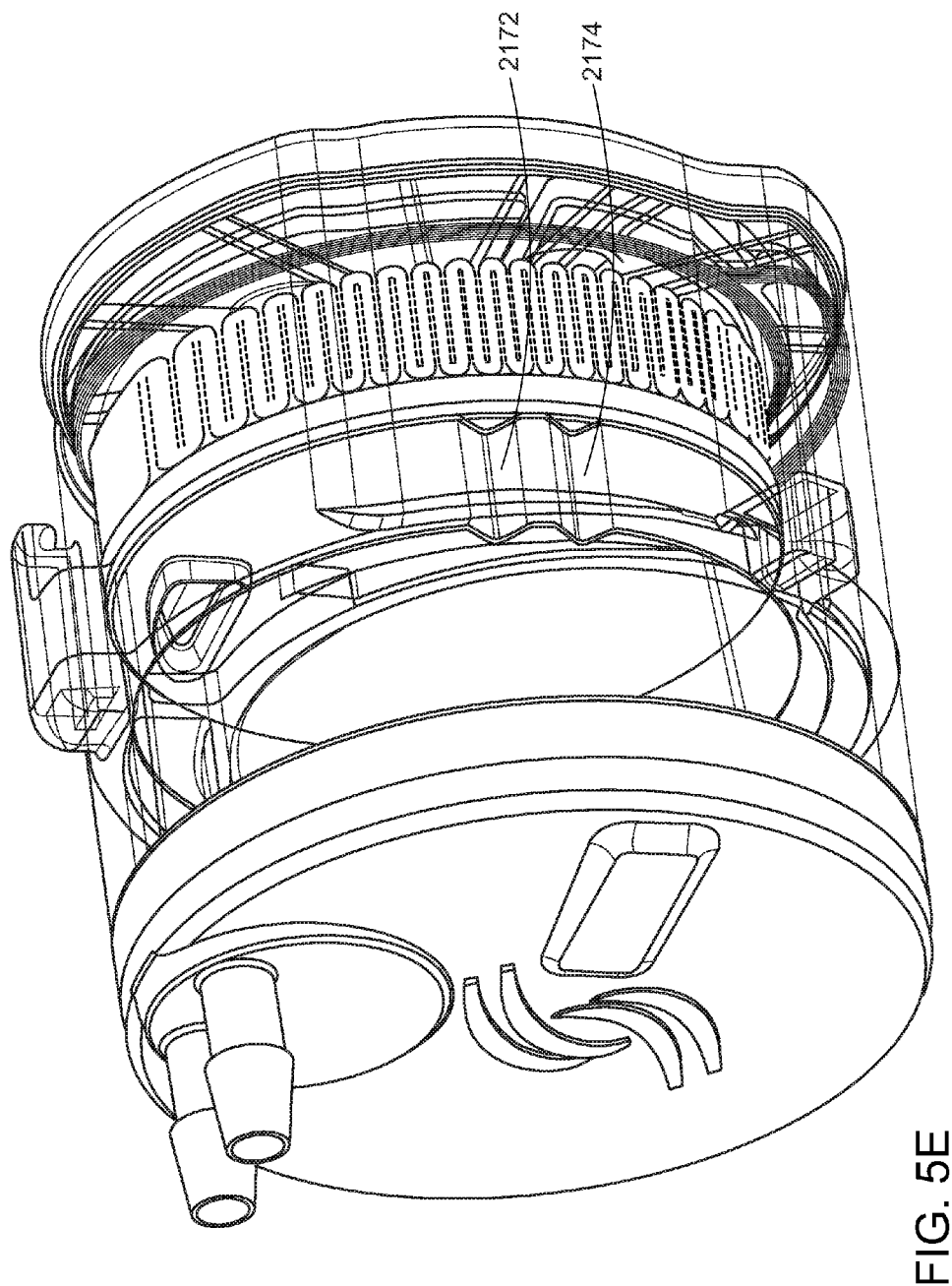
Figure 5G:
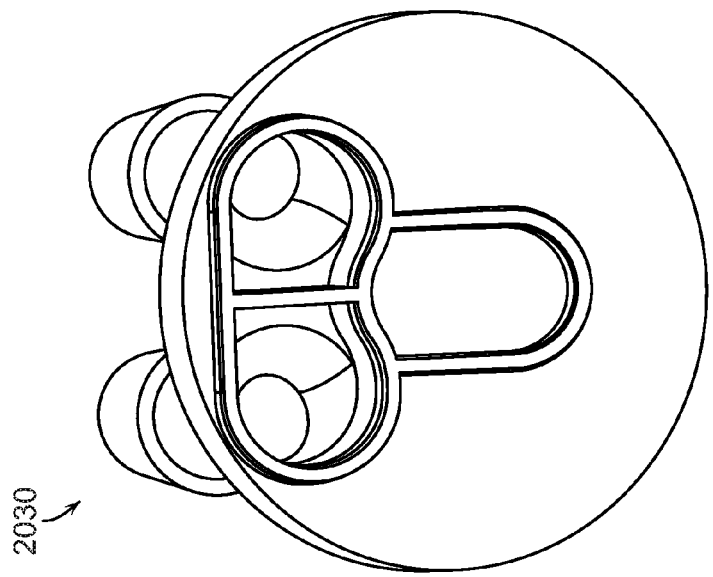
Figure 5F:
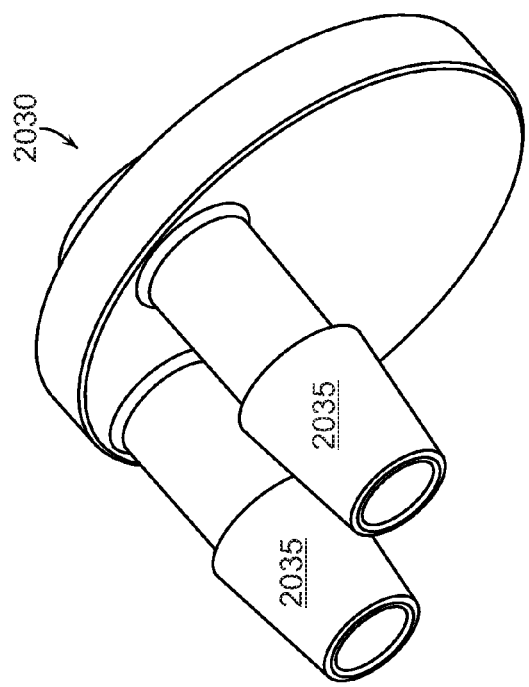
Figure 5I:
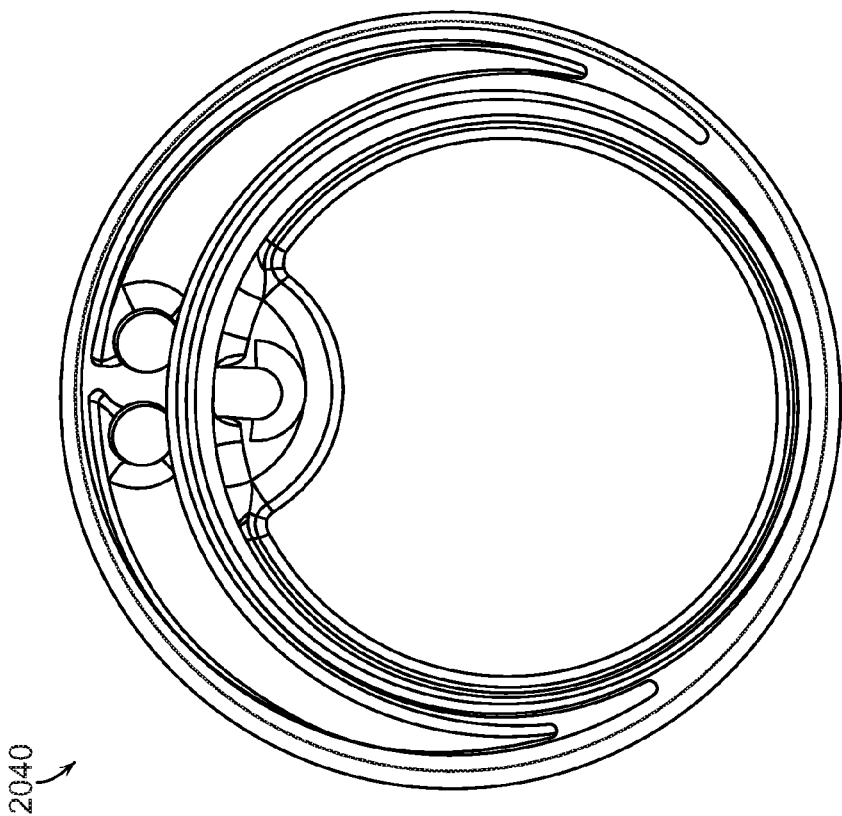
Figure 5H:
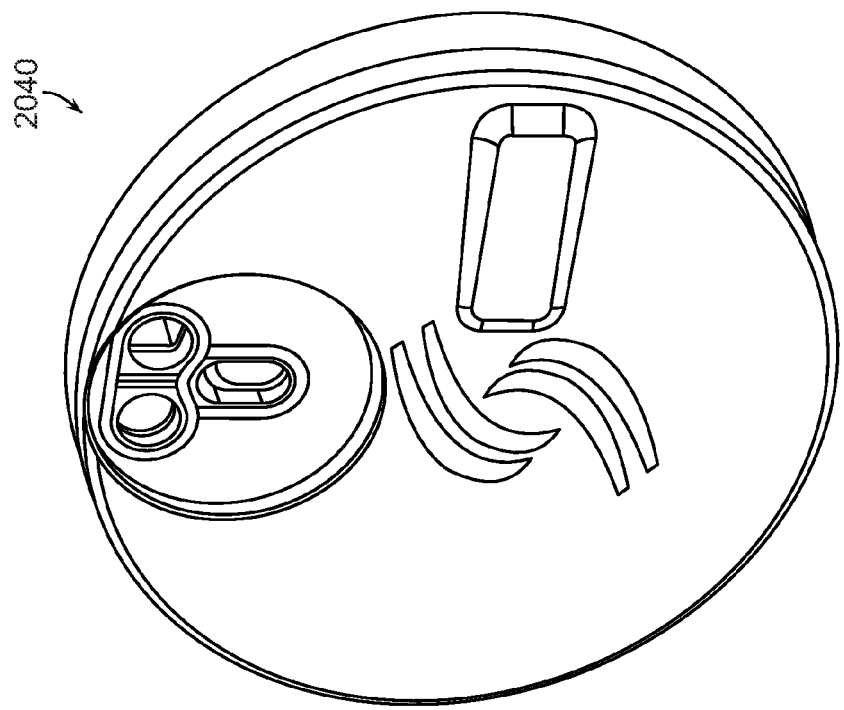
Figure 5J:
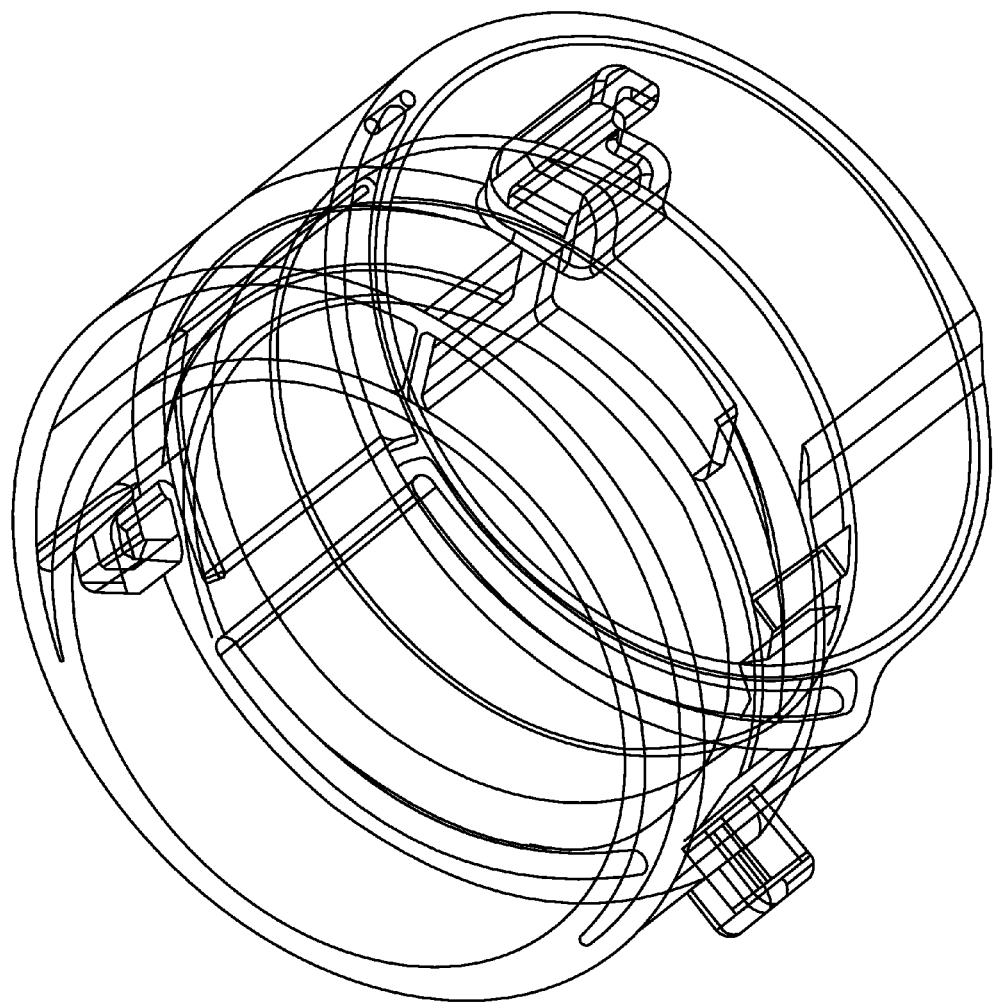
Figure 5K:
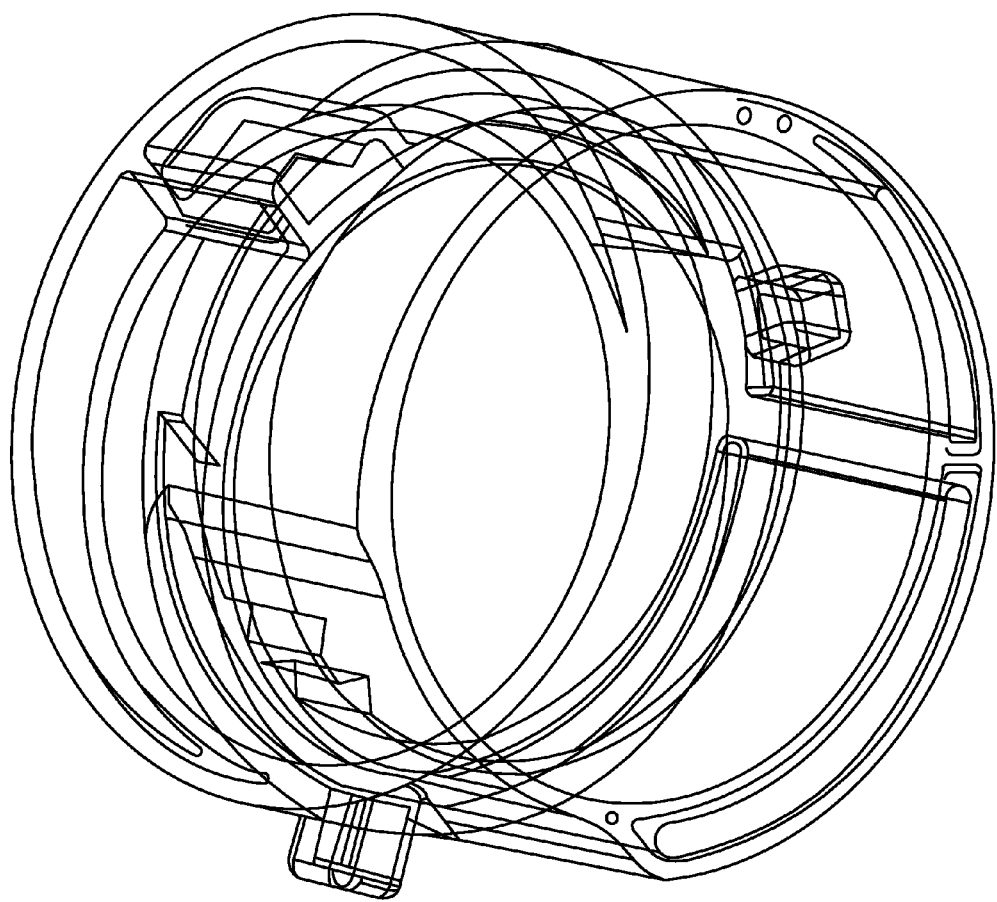
Figure 5L:
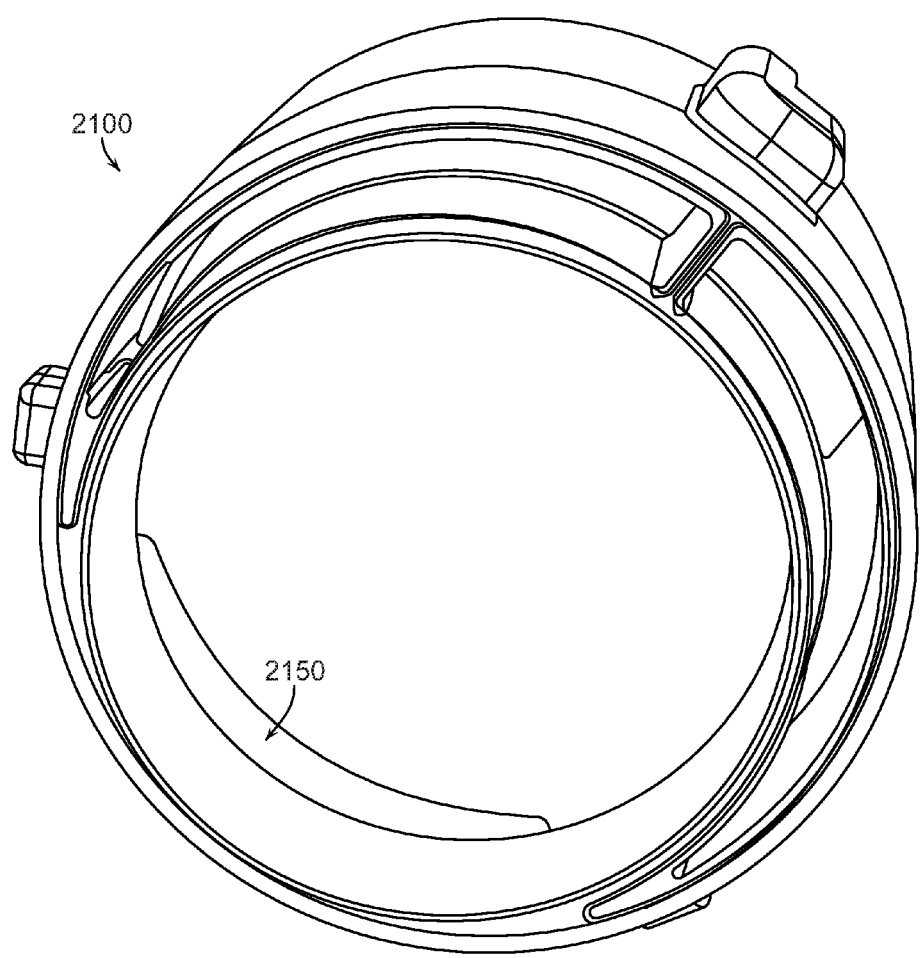
Figure 5M:
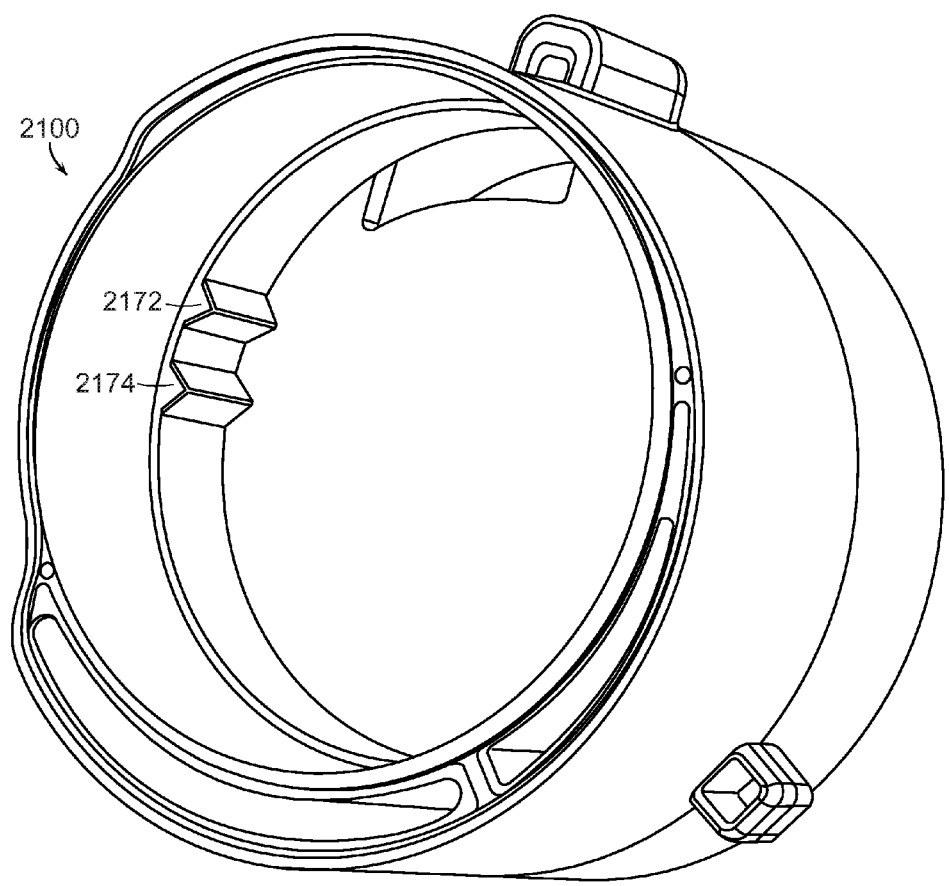
Figure 5N:
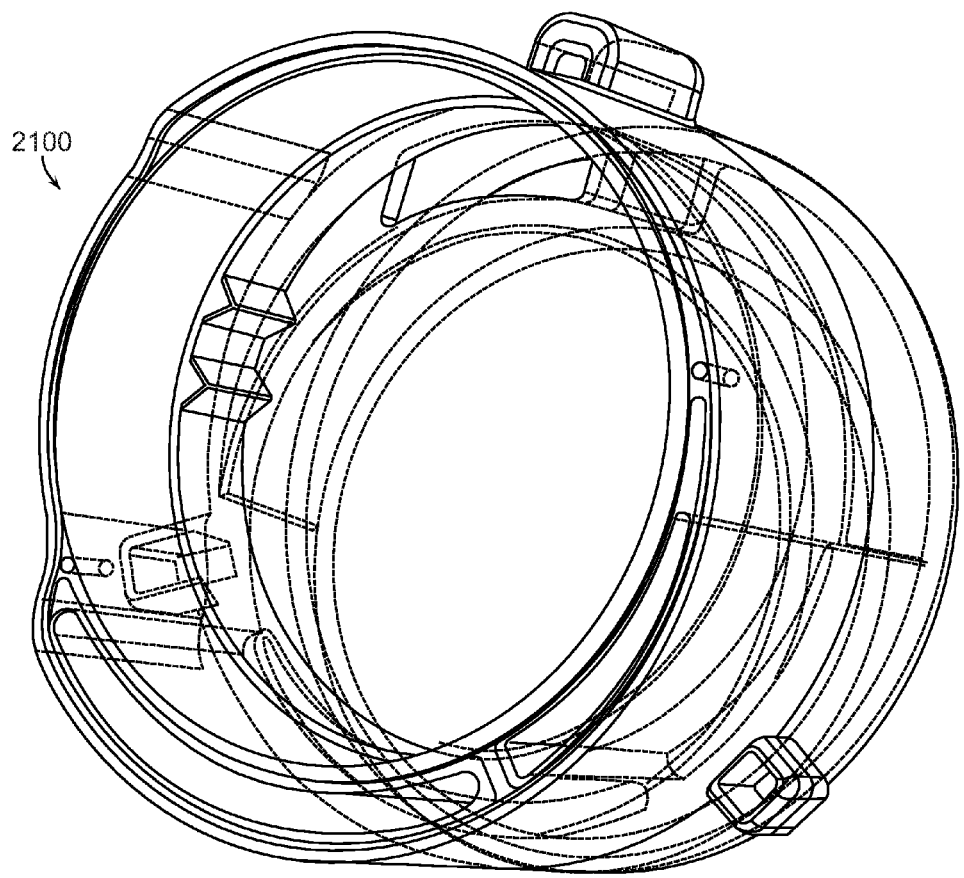
Figure 5O:
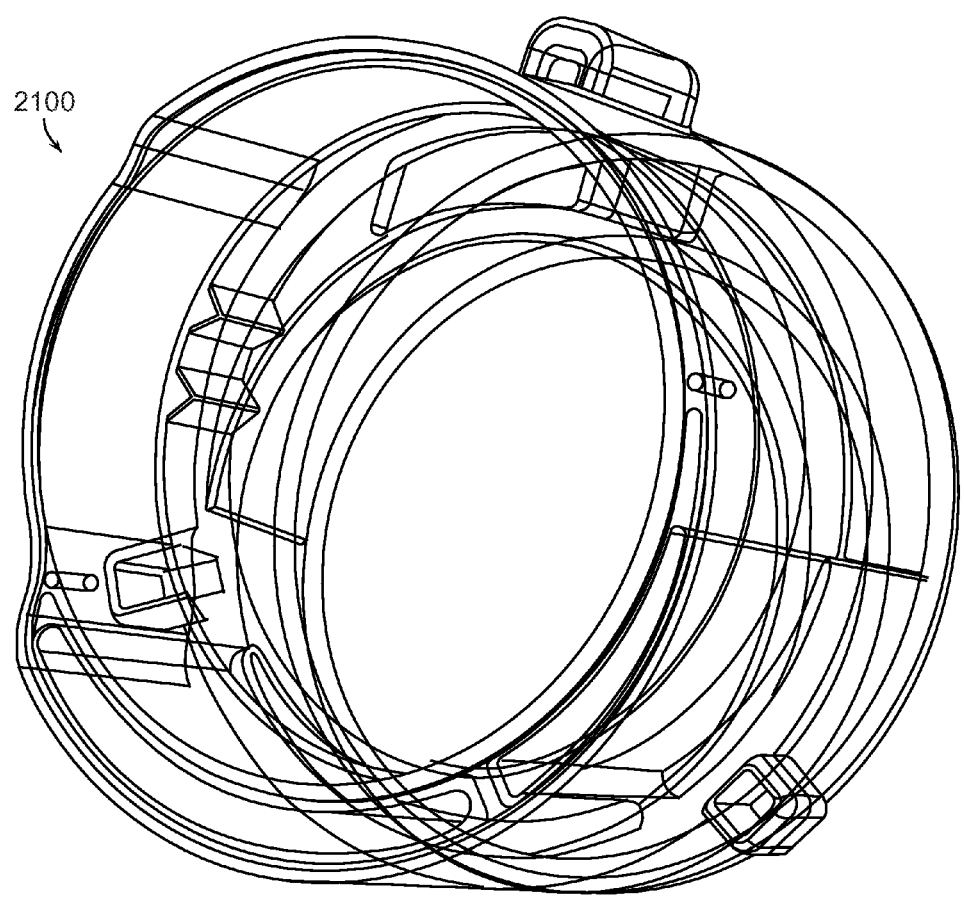
Figure 5Q:
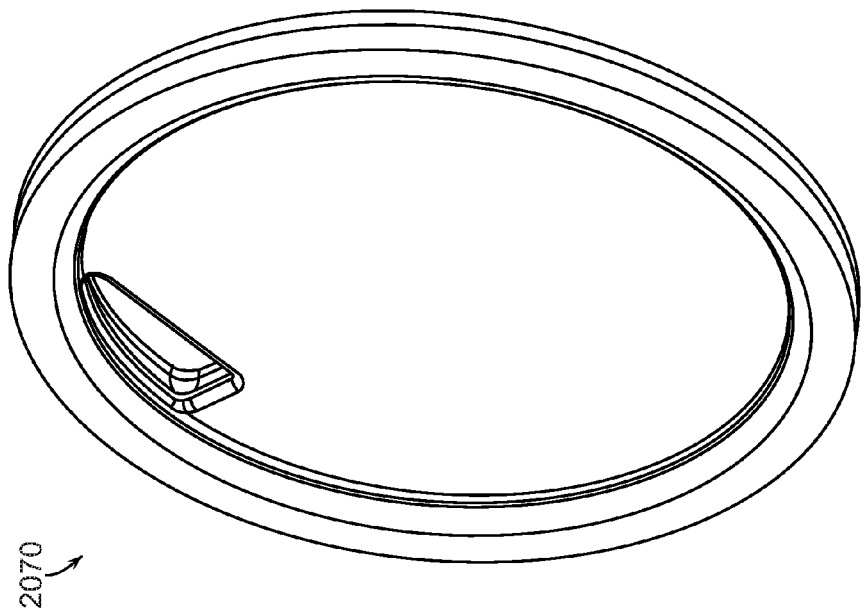
Figure 5P:
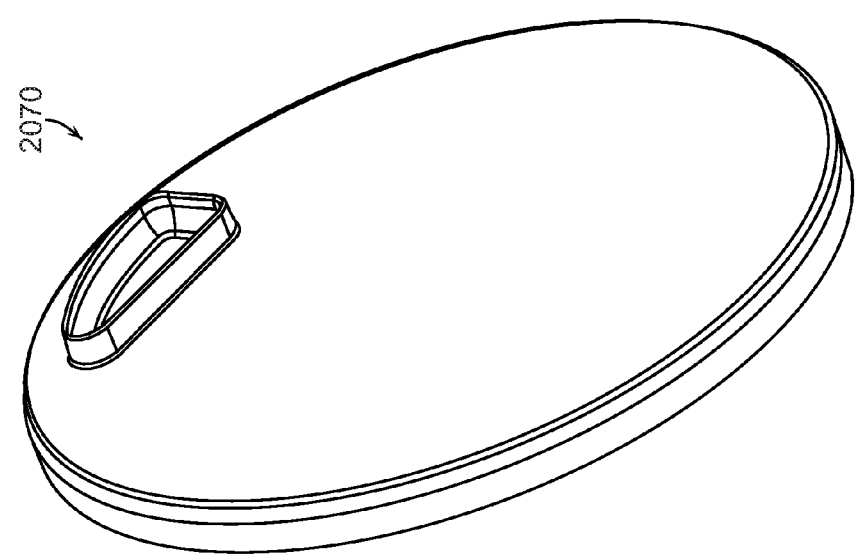
Figure 5R:
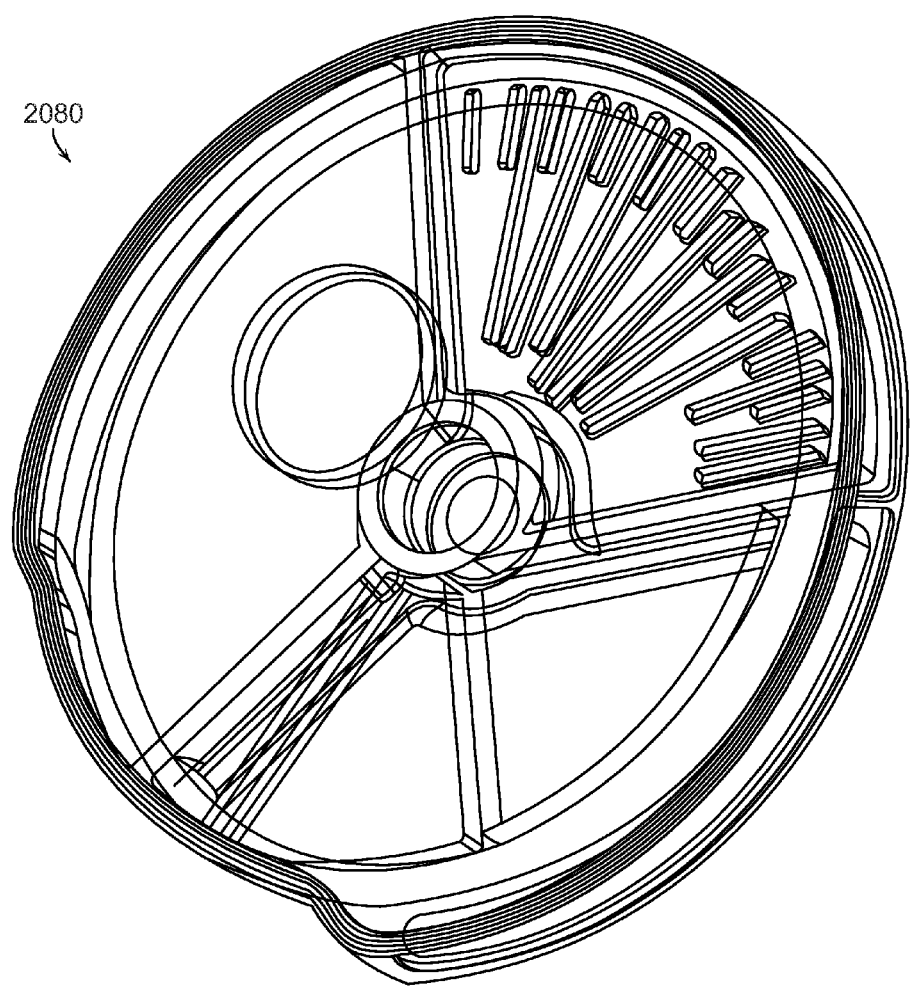
Figure 5T:
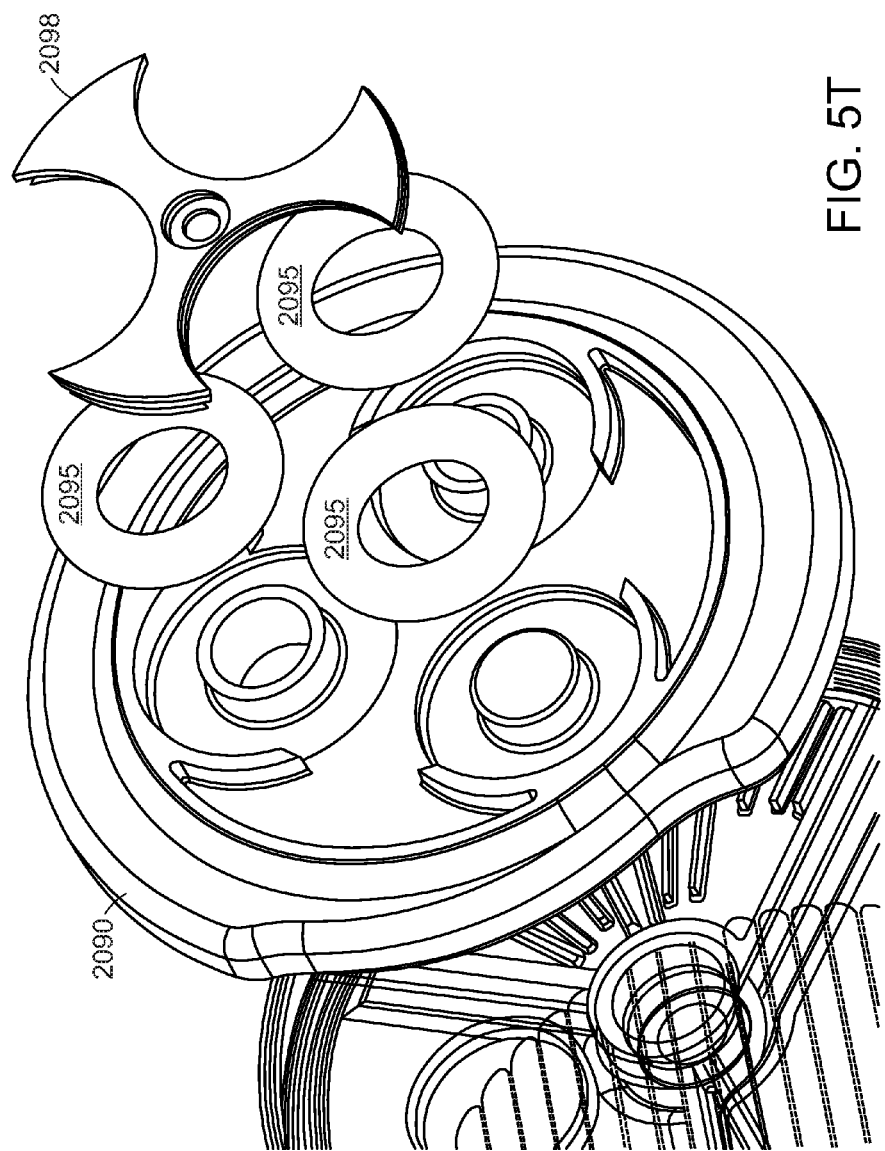

A second embodiment of filter 2000 is presented in FIGS. 5(A)-5(T), wherein like numbers refer to like components of filter 1000, but with a prefix of 2. Filter 2000 shares many similarities in components with filter 1000, but provides only two fluid flow paths/plena rather than three. Specifically, the fluid passages 1220, 1230 of filter 1000 remain essentially unchanged, but fluid passage 1210 and its associated filter 1050 are eliminated. One intended use of filter 2000 is for purposes of smoke evacuation, particularly when an air-actuated trocar (as described herein) is not connected to the system. Manifold 2030 differs from manifold 1030, in that it includes two fluid passages instead of three, defined by bosses 2035 that are adapted and configured to receive flexible tubing thereon from the tube set.

Referring back to FIGS. 1B, 2 and 3, the system 100 of FIG. 1B includes an additional dump valve 115 in connection with the fluid supply conduit 114. In addition to the short-circuiting action of the back-pressure control valve 113 described above, the system 100 is provided with a pressure sensor 117, which can be mechanical but is, as illustrated, electronic. The pressure sensor 117, if provided, is in fluid communication with the insufflation conduit 118 or other source of abdominal pressure. When an over-pressure condition is sensed, the pressure sensor 117 signals the dump valve 115 to release fluid out of the system 100. As illustrated, the dump valve 115 is electro-mechanical, but alternatively may be fully mechanical, as desired.

It is to be appreciated one or more additional dump valves (e.g. dump valve 119) can be provided to reduce any possibility of overpressure conditions, and/or to provide redundancy for other safety features.

In the embodiment of FIG. 1B, the system 100 operates, as set forth above, but is not to be understood to be limited thereto, with one surgical device 131 being used for insufflation and sensing functions, another surgical device 135 serving to remove insufflation gas from the abdomen, which then passes through a filter, such as an ultralow-penetration air ("ULPA") filter element 116 for example, before returning to the pump 111. The filter 116 is preferably configured and adapted to clear all or essentially all smoke and debris from the gas passing therethrough, with the gas being returned to the abdominal cavity 190 through a third surgical device 133. As illustrated, another filter element 116 can be provided in connection with the supply conduit 114 leading from the pump 111.

For the purposes of explanation and illustration, and not limitation, a schematic illustration of an exemplary embodiment of a surgical gas delivery system in accordance with another aspect of the invention is shown in FIG. 2 and is designated generally by reference character 200. As compared with the system 100 of FIG. 1B, the system 200 only requires two surgical devices (e.g., cannulas). The functionalities of components described above in connection with the system 100 of FIG. 1B are the same as the corresponding components of the system 200 of FIG. 2, unless otherwise specified.

The system 200 is in many ways similar to the system 100 of FIG. 1B, but with the addition of a diverting valve 295, having three conduits 112, 114, 118 leading from other active internal system components, and two conduits 251, 253 leading, respectively, to two different surgical devices 231, 233.

As illustrated, the diverting valve 295 is provided integrally, within the control unit 210, as indicated schematically by placement of broken line referenced by number 210. The diverting valve is provided with three positions—positions, A, B and C, corresponding to different functions, as described below. When the sensing function of the system 200 is active, the diverting valve 295 is positioned in, as illustrated, position "A", permitting connection of the insufflation/sensing conduit 118 therethrough, through one or both of the conduits 251, 253 of the tube set 250, and to one or both of the surgical devices 231, 233. If configured to connect the insufflation/sensing conduit 118 to more than one surgical device, the potential for a lumen of such surgical device being blocked and thus not providing an accurate reading, is reduced. When the diverting valve 295 is positioned at position A, and connects the insufflation/sensing conduit 118 to the conduits 251, 253 of the tube set 250 and thus to the surgical devices 231, 233, the insufflator subunit 121 is permitted to sense the abdominal pressure. In position A, output from the pump 111 enters the diverting valve 295 and is returned to the pump 111 immediately by mutually connecting the supply conduit 114 and return conduit 112 under such circumstances. This configuration allows the pump 111 to continue running during sensing and thus avoids any power spikes which might occur if stopping and restarting of the pump 111.

If the system 200 is set to a suitable mode (such as combined smoke evacuation and insufflation), when the insufflator subunit 121 is finished sensing the abdominal pressure, the diverting valve 295 is switched from position A, to Position B, in order to connect the supply conduit 114 to a corresponding conduit 251 of the tube set 250, and the return conduit 112 to a corresponding conduit 253 of the tube set 250. In position B, the insufflator conduit 118 is connected to the return conduit 112, permitting addition of insufflation gas into the system 200 through the return conduit 112. Concurrently, the insufflator subunit 121 can be set to insufflating mode only, therefore only adding gas to the system 200 and not sensing pressures.

While in position B, the diverting valve 295 permits delivery and return of fluid therethrough, between the pump 111 and filters 216, and the surgical devices 231, 233, and therefore gas exchange with, and filtration of, insufflation gasses from the surgical cavity 190.

If the pump and tube volume are considered as one controlled volume in conjunction with the volume of the surgical cavity 190, the function of the insufflator subunit 121 alone—switching from sensing to supplying carbon dioxide—is performed as in conventional surgical insufflators, in accordance with a preferred aspect.

Accordingly, as described above, in the system 200 of FIG. 2, smoke evacuation and filtration is only performed when the diverting valve 295 permits the insufflator control 121 to provide gas to the surgical cavity 190. In such an arrangement, toggling to and from smoke evacuation/filtration and pressure sensing can be configured as either a normally sensing mode, or as a normally filtering mode, as desired or required. A normally sensing mode is likely to be preferred over a normally filtering mode, as monitoring of abdominal pressures is typically a priority.

As illustrated, position C of the diverting valve 295 permits the system 200 to be operated in a recirculation mode, the recirculation mode being suitable for providing sufficient pressures and flow rates to drive surgical access devices such as those described in U.S. Patent Publication No. 2007/0088275, as well as in U.S. Patent Application Ser. No. 61/104,448, filed Oct. 10, 2008, and/or those described in U.S. Pat. Nos. 7,182,752, 7,285,112, 7,413,559 or 7,338,473, for example. In such a mode, a single tube of three lumens is typically provided, one lumen being in fluid communication with each of the supply conduit 112, return conduit 114 and the insufflation conduit 118.

For the purposes of explanation and illustration, and not limitation, a schematic illustration of an exemplary embodiment of a surgical gas delivery system in accordance with still another aspect of the invention is shown in FIG. 3 and is designated generally by reference character 300.

The functionality of components described above in connection with the systems 100 and 200 of FIGS. 1B and 2, respectively are the same as the corresponding components of the system 300 of FIG. 3, unless otherwise specified.

As with the system 200 of FIG. 2, the system 300 of FIG. 3 utilizes two separate fluid conduits 251, 253 to surgical devices 231, 233, which are in fluid communication with the surgical cavity 190. Instead of a single insufflation/sense conduit 118, in the system 200 of FIG. 2, a separate pressure sense conduit 318a and an insufflation fluid conduit 318b are provided. The pressure sense and insufflation fluid conduits 318a, 318b are provided in connection with the insufflation subunit 121, through one or more filters 216, and into a diverting valve 395. A supply conduit 114 and return conduit 112 provided in connection with the pump 111 are also fed into the diverting valve 395. This arrangement permits continuous addition of insufflation gas from the supply 140, if necessary.

As illustrated, the diverting valve 395 is provided with three positions, A, B and C. As illustrated in FIG. 3, in valve 395 position C, the pressure sense conduit 318a and insufflation fluid conduit 318b are connected respectively to the two external fluid conduits 253, 251, to respective surgical devices (e.g. 233, 231), pressure sensing being accomplished through one surgical device (e.g. 233), while flow of insufflation gas is carried through the other conduit (e.g. 251) to the other surgical device (e.g., 231). Also in position C, the supply 114 and return 112 conduits are placed in fluid communication, bypassing the surgical devices 231, 233. Thus, the pump 111 may continue running and be re-activated in the system 300 by change in position of the valve 395. In this manner, power spikes are avoided with repeated starting and stopping of the pump 111.

As illustrated, the diverting valve 395 is provided integrally, within the control unit 310, behind filters 216, as schematically illustrated by placement of the broken line, referenced by element number 310.

When the insufflator control 121 is not sensing, the diverting valve 395 is positioned in position B, in which the conduits 251, 253 and surgical devices 231, 233 are placed in fluid connection, through the diverting valve 395, with the supply conduit 114 and return conduit 112, and thus with the pump 111, in order to provide smoke removal function, for example. With valve 395 in position B, the pressure sense conduit 318a terminates at the valve 395. In position B, supply of insufflation fluid can be provided by the insufflation subunit 121, through the insufflation conduit 318b, to the return line 112 to the pump 111, by way of the diverting valve 395, permitting continuous addition of insufflation gas to the system 300, if necessary. By providing insufflation gas to the return line 112 to the pump 111, insufflation gas is injected into the controlled volume of the abdomen through the return line 112, to the pump 111. Alternatively, if so-desired, addition of insufflation gas can be provided on the supply conduit 114 side of the pump 111.

In accordance with the invention, it is conceived that the rate of flow, which can be controlled by a user, is achieved, in one aspect, by the back-pressure control valve 113, which can be embodied as an electro-mechanical valve to enable interface with an electronic control system, for example.

In general, flow to and from the surgical devices 231, 235 for smoke evacuation/filtration functions will not solely affect pressure in the surgical cavity 190, because absent addition of gas by the insufflation subunit 121, only insufflation gas removed from the abdomen will be returned to the abdomen, and at the same flow rate. Otherwise, the pump 111 would become "starved."

As illustrated, position A of the diverting valve 395 permits the system 300 to be operated in a recirculation mode, the recirculation mode being suitable for providing sufficient pressures and flow rates to drive surgical access devices such as those described in U.S. Patent Publication No. 2007/0088275, as well as in U.S. Patent Application Ser. No. 61/104,448, filed Oct. 10, 2008, and/or those described in U.S. Pat. Nos. 7,182,752, 7,285,112, 7,413,559 or 7,338,473, for example. In such a mode, a single tube of three lumens is typically provided, one lumen being in fluid communication with each of the supply conduit 112, return conduit 114 and the insufflation conduit 118.

In accordance with the invention, it is conceived that the rate of flow for smoke evacuation may be considerably less than the amount of flow used to power surgical access devices, such as those described in U.S. Pub. No. 2007/0088275 and U.S. 61/104,448, filed Oct. 10, 2008, for example. For example, if flow rates are excessively high, gas turbulence in the surgical cavity 190 may occur. Accordingly, integral flow restriction elements provided in connection with the tube sets 150, 250 or filter(s) 16 may be necessary to help reduce filtered gas flow.

It is to be understood that features of any embodiment described herein can be provided in connection with any other embodiment described herein, even if not explicitly described in connection with such embodiment, unless such features would be mutually exclusive. It will be apparent to those skilled in the art that still further modifications and variations can be made in the subject systems, devices and methods without departing from the spirit or scope of the invention.

What is claimed is:

1. A multimodal surgical gas delivery system configured for use with one or more trocars providing access into a patient's body cavity, the system comprising:
   a control unit having a pump with a supply conduit and a return conduit, an insufflation subunit with an insufflation conduit, and a diverting valve having a plurality of defined operating positions and connected to each of the supply conduit, the return conduit and the insufflation conduit for controlling gas flow through the gas delivery system based upon a user selected operating mode, and wherein the control unit has multiple user selectable operating modes including:
   i) a recirculation mode wherein the diverting valve is positioned to facilitate the delivery of pressurized gas from the pump, through the supply conduit, to a trocar of the one or more trocars, to create and maintain a pressure barrier therein which inhibits a loss of insufflation gas from the patient's body cavity through the trocar of the one or more trocars, wherein depressurized gas from the pressure barrier created in the trocar returns to the pump through the return conduit;
   ii) a smoke evacuation mode wherein the diverting valve is positioned to facilitate the removal of smoke from the insufflation gas within the patient's body cavity to improve visibility within the patient's body cavity; and
   iii) an insufflation mode wherein the diverting valve is positioned to facilitate the delivery of insufflation gas into the patient's body cavity from the insufflation subunit, through the insufflation conduit, to create and maintain a pneumoperitoneum,
   wherein the control unit is configured to permit a user to select an operating mode either individually or combined with another operating mode.

2. The multimodal surgical gas delivery system as recited in claim 1, wherein the control unit includes a control panel to permit the user to select an operating mode either individually or combined with another operating mode.

3. The multimodal surgical gas delivery system as recited in claim 1, wherein the control panel is configured to permit the user to selectively adjust operation parameters of each of the operating modes.

4. The multimodal surgical gas delivery system as recited in claim 1, wherein the control unit includes a pressure sensor for sensing abdominal pressure through the insufflation conduit.

5. The multimodal surgical gas delivery system as recited in claim 1, wherein the control unit includes a back-pressure control valve in communication with the supply conduit and the return conduit configured to respond to a supply conduit pressure exceeding a set pressure by directing gas from the supply conduit to the return conduit.

6. The multimodal surgical gas delivery system as recited in claim 1, further comprising a filter element configured to filter gas returning to the pump through the return conduit.

7. The multimodal surgical gas delivery system as recited in claim 1, further comprising a filter element configured to filter gas delivered by the pump through the supply conduit.

8. The multimodal surgical gas delivery system as recited in claim 1, further comprising a filter element configured to filter gas delivered from the insufflation subunit through the insufflation conduit.

* * * * *